United States Patent
Thomas et al.

(10) Patent No.: US 9,289,302 B2
(45) Date of Patent: Mar. 22, 2016

(54) MOSAICPLASTY CONSTRUCTS

(75) Inventors: Brian H. Thomas, Columbia City, IN (US); Steven J. Charlebois, West Lafayette, IN (US); Donald Yakimicki, Warsaw, IN (US); James Mason, Granger, IN (US); Stephen H. Spiegelberg, Winchester, MA (US); Gavin Braithwaite, Cambridge, MA (US); Gareth McKinley, Acton, MA (US); Orhun Muratoglu, Cambridge, MA (US)

(73) Assignee: Zimmer, Inc., Warsaw, IN (US)

( * ) Notice: Subject to any disclaimer, the term of this patent is extended or adjusted under 35 U.S.C. 154(b) by 1306 days.

(21) Appl. No.: 12/505,583

(22) Filed: Jul. 20, 2009

(65) Prior Publication Data

US 2010/0161073 A1 Jun. 24, 2010

Related U.S. Application Data

(60) Provisional application No. 61/084,121, filed on Jul. 28, 2008.

(51) Int. Cl.
*A61F 2/08* (2006.01)
*A61F 2/30* (2006.01)
(Continued)

(52) U.S. Cl.
CPC ..... *A61F 2/30756* (2013.01); *A61F 2002/2817* (2013.01); *A61F 2002/2839* (2013.01);
(Continued)

(58) Field of Classification Search
CPC .............. A61F 2/2846; A61F 2/30907; A61F 2002/2835; A61F 2002/2839; A61F 2002/285; A61F 2002/30563; A61F 2002/30733; A61F 2002/30751; A61F 2002/30014; A61F 2002/30016; A61F 2002/30029; A61F 2002/30965; A61F 2002/30057; A61F 2002/30006; A61F 2002/30008; A61F 2002/3007; A61F 2002/30075; A61F 2002/30317; A61F 2002/30911; A61F 2002/3092; A61F 2002/3093; A61F 2002/30759; A61F 2002/30761; A61F 2002/30756; A61F 2310/00131
USPC ............. 623/14.12, 23.48, 23.5, 23.51, 23.55
See application file for complete search history.

(56) References Cited

U.S. PATENT DOCUMENTS

RE31,865 E * 4/1985 Roux ........................ A61F 2/32
623/22.14
5,108,446 A * 4/1992 Wagner et al. ............. 623/22.28
(Continued)

FOREIGN PATENT DOCUMENTS

WO WO-2010014446 A1 2/2010

OTHER PUBLICATIONS

The Written Opinion and International Search Report mailed Nov. 4, 2009 in related International Application No. PCT/US2009/051098.
(Continued)

*Primary Examiner* — Thomas J Sweet
*Assistant Examiner* — Cheryl Miller
(74) *Attorney, Agent, or Firm* — Schwegman Lundberg & Woessner, P.A.

(57) ABSTRACT

Various embodiments of mosaicplasty constructs and methods for implanting the constructs into anatomical structures. The mosaicplasty constructs may be formed from artificial materials and may include a hard articulating portion and a relatively softer elastic, support portion. The mosaicplasty constructs may include bone ingrowth materials to facilitate ingrowth of bone and other tissues into the construct. The mosaicplasty constructs may also be at least partially formed of hydrogel materials.

9 Claims, 11 Drawing Sheets

(51) Int. Cl.
  *A61F 2/28* (2006.01)
  *A61F 2/44* (2006.01)
  *A61F 2/46* (2006.01)

(52) U.S. Cl.
  CPC ... *A61F2002/305* (2013.01); *A61F 2002/3013* (2013.01); *A61F 2002/30016* (2013.01); *A61F 2002/3021* (2013.01); *A61F 2002/30057* (2013.01); *A61F 2002/30069* (2013.01); *A61F 2002/30075* (2013.01); *A61F 2002/3092* (2013.01); *A61F 2002/30112* (2013.01); *A61F 2002/30153* (2013.01); *A61F 2002/30156* (2013.01); *A61F 2002/30163* (2013.01); *A61F 2002/30224* (2013.01); *A61F 2002/30232* (2013.01); *A61F 2002/30245* (2013.01); *A61F 2002/30247* (2013.01); *A61F 2002/30331* (2013.01); *A61F 2002/30448* (2013.01); *A61F 2002/30467* (2013.01); *A61F 2002/30563* (2013.01); *A61F 2002/30574* (2013.01); *A61F 2002/30677* (2013.01); *A61F 2002/30759* (2013.01); *A61F 2002/30772* (2013.01); *A61F 2002/30937* (2013.01); *A61F 2002/30971* (2013.01); *A61F 2002/4495* (2013.01); *A61F 2002/4631* (2013.01); *A61F 2210/0061* (2013.01); *A61F 2220/005* (2013.01); *A61F 2220/0025* (2013.01); *A61F 2220/0033* (2013.01); *A61F 2220/0083* (2013.01); *A61F 2230/001* (2013.01); *A61F 2230/0004* (2013.01); *A61F 2230/0019* (2013.01); *A61F 2230/0023* (2013.01); *A61F 2230/0028* (2013.01); *A61F 2230/0067* (2013.01); *A61F 2230/0069* (2013.01); *A61F 2230/0071* (2013.01); *A61F 2250/0019* (2013.01); *A61F 2310/00011* (2013.01); *A61F 2310/00131* (2013.01); *A61F 2310/00179* (2013.01)

(56) References Cited

U.S. PATENT DOCUMENTS

| | | | |
|---|---|---|---|
| 5,735,905 A * | 4/1998 | Parr | A61F 2/3609 623/23.11 |
| 5,921,946 A | 7/1999 | Tillinghast et al. | |
| 6,096,083 A * | 8/2000 | Keller | A61F 2/32 623/18.11 |
| 6,126,695 A * | 10/2000 | Semlitsch | 623/22.15 |
| 6,197,061 B1 | 3/2001 | Masuda et al. | |
| 6,206,927 B1 | 3/2001 | Fell et al. | |
| 6,231,605 B1 | 5/2001 | Ku | |
| 6,306,142 B1 | 10/2001 | Johanson et al. | |
| 6,451,060 B2 | 9/2002 | Masuda et al. | |
| 6,520,964 B2 | 2/2003 | Tallarida et al. | |
| 6,528,052 B1 | 3/2003 | Smith et al. | |
| 6,558,421 B1 | 5/2003 | Fell et al. | |
| 6,585,647 B1 | 7/2003 | Winder | |
| 6,610,067 B2 | 8/2003 | Tallarida et al. | |
| 6,620,185 B1 | 9/2003 | Harvie et al. | |
| 6,623,963 B1 | 9/2003 | Muller et al. | |
| 6,626,945 B2 | 9/2003 | Simon et al. | |
| 6,632,246 B1 | 10/2003 | Simon et al. | |
| 6,679,917 B2 | 1/2004 | Ek | |
| 6,689,747 B2 | 2/2004 | Filvaroff et al. | |
| 6,727,224 B1 | 4/2004 | Zhang et al. | |
| 6,767,354 B2 | 7/2004 | Johanson et al. | |
| 6,852,125 B2 | 2/2005 | Simon et al. | |
| 6,858,042 B2 | 2/2005 | Nadler et al. | |
| 6,932,308 B2 | 8/2005 | Talish et al. | |
| 7,029,479 B2 | 4/2006 | Tallarida et al. | |
| 7,049,248 B2 | 5/2006 | Lee et al. | |
| 7,067,123 B2 | 6/2006 | Gomes et al. | |
| 7,108,663 B2 | 9/2006 | Talish et al. | |
| 7,144,414 B2 | 12/2006 | Harvie et al. | |
| 7,148,209 B2 | 12/2006 | Hoemann et al. | |
| 7,153,307 B2 | 12/2006 | Scribner et al. | |
| 7,156,880 B2 | 1/2007 | Evans | |
| 7,163,541 B2 | 1/2007 | Ek | |
| 7,166,133 B2 | 1/2007 | Evans | |
| 7,211,060 B1 | 5/2007 | Talish | |
| 7,217,294 B2 | 5/2007 | Kusanagi et al. | |
| 7,635,447 B2 * | 12/2009 | Hamman et al. | 419/2 |
| 8,226,728 B2 * | 7/2012 | Preuss | A61F 2/34 623/22.14 |
| 2002/0099446 A1 * | 7/2002 | MacArthur | A61F 2/30756 623/20.14 |
| 2003/0060887 A1 | 3/2003 | Ek | |
| 2004/0098127 A1 * | 5/2004 | Charlebois | A61F 2/389 623/16.11 |
| 2004/0162622 A1 * | 8/2004 | Simon et al. | 623/23.5 |
| 2004/0171740 A1 | 9/2004 | Ruberti et al. | |
| 2004/0195727 A1 * | 10/2004 | Stoy | 264/319 |
| 2005/0064042 A1 | 3/2005 | Vunjak-Novakovic et al. | |
| 2005/0112397 A1 * | 5/2005 | Rolfe | A61B 17/8605 428/593 |
| 2005/0123672 A1 * | 6/2005 | Justin | A61C 8/0012 427/2.26 |
| 2005/0273178 A1 * | 12/2005 | Boyan | A61F 2/442 623/23.74 |
| 2005/0287187 A1 * | 12/2005 | Mansmann | 424/423 |
| 2006/0178748 A1 * | 8/2006 | Dinger, III | A61B 17/1615 623/18.11 |
| 2006/0235542 A1 * | 10/2006 | Hodorek et al. | 623/23.51 |
| 2006/0247790 A1 | 11/2006 | McKay | |
| 2007/0100450 A1 * | 5/2007 | Hodorek | 623/14.12 |
| 2007/0179607 A1 * | 8/2007 | Hodorek et al. | 623/14.12 |
| 2007/0185585 A1 | 8/2007 | Bracy et al. | |
| 2008/0065210 A1 | 3/2008 | McKay | |
| 2008/0097606 A1 * | 4/2008 | Cragg | A61F 2/3872 623/14.12 |
| 2008/0249632 A1 | 10/2008 | Stone et al. | |
| 2008/0262626 A1 * | 10/2008 | Raugel | A61F 2/30734 623/22.15 |
| 2009/0043398 A1 | 2/2009 | Yakimicki et al. | |
| 2010/0049321 A1 * | 2/2010 | Lower et al. | 623/14.12 |

OTHER PUBLICATIONS

Webpage: http://guidance.nice.org.uk/IPG162—Masaicplasty for knee cartilage defects, National Institute for Health and Clinical Excellence (NHS-Mosaicplasty), printed Jul. 17, 2009.
"European Application Serial No. 09790615.0, Non-Final Office Action mailed Jun. 16, 2011", 1 pg.
"European Application Serial No. 09790615.0, Non-Final Office Action mailed Jun. 22, 2011", 1 pg.
"European Application Serial No. 09790615.0, Non-Final Office Action mailed Jul. 12, 2011", 1 pg.
"European Application Serial No. 09790615.0, Office Action mailed Mar. 26, 2012", 1 pg.
"European Application Serial No. 09790615.0, Office Action mailed May 23, 2011", 2 pg.
"International Application Serial No. PCT/US2009/051098, International Preliminary Report on Patentability mailed Feb. 1, 2011", 8 pgs.

* cited by examiner

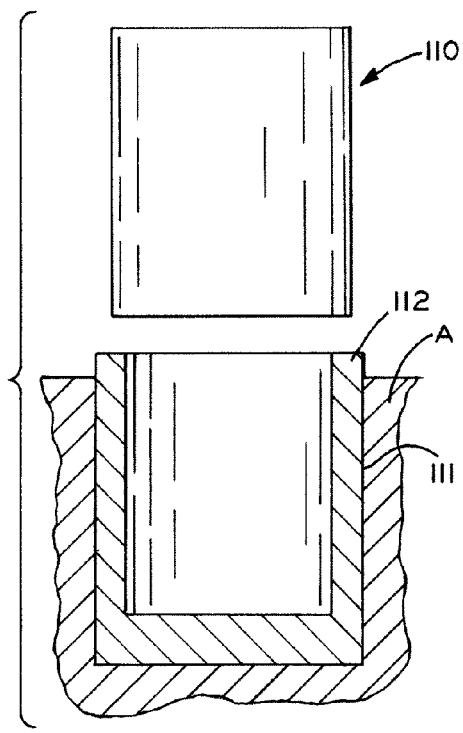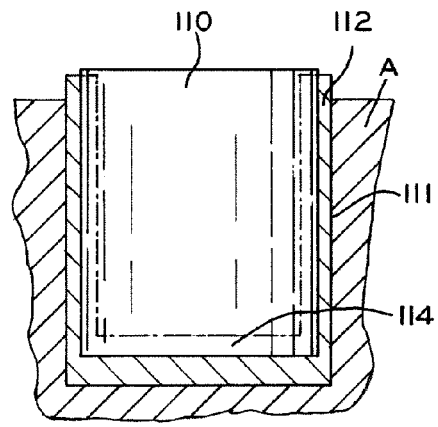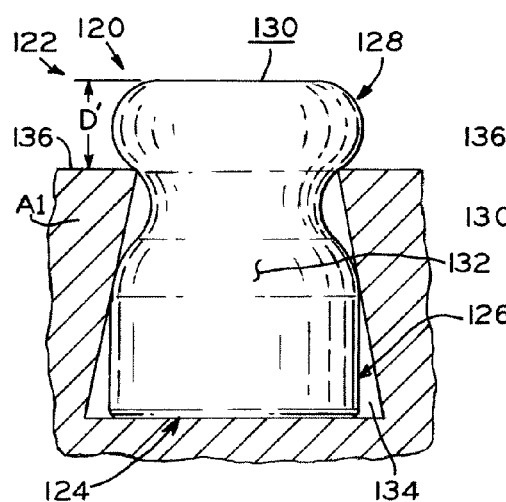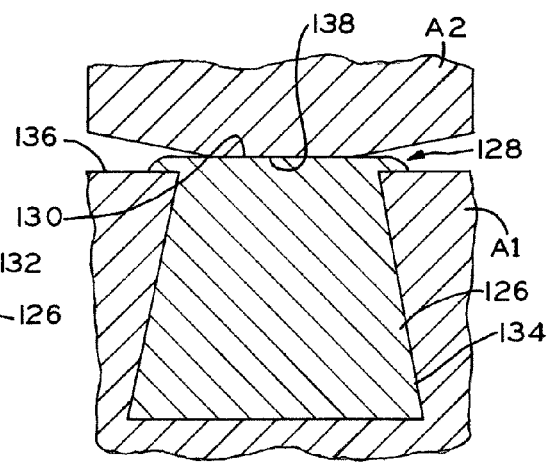
FIG_11    FIG_12    FIG_13    FIG_14

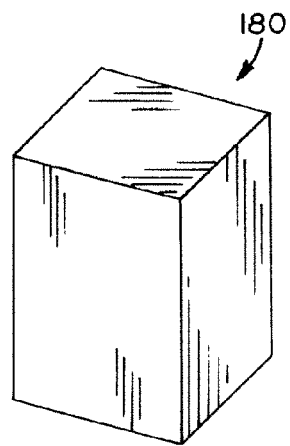 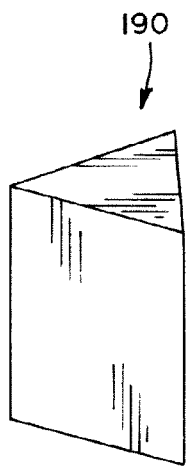 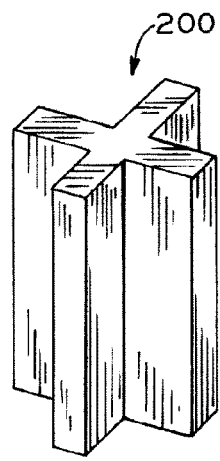
FIG. 21  FIG. 22  FIG. 23
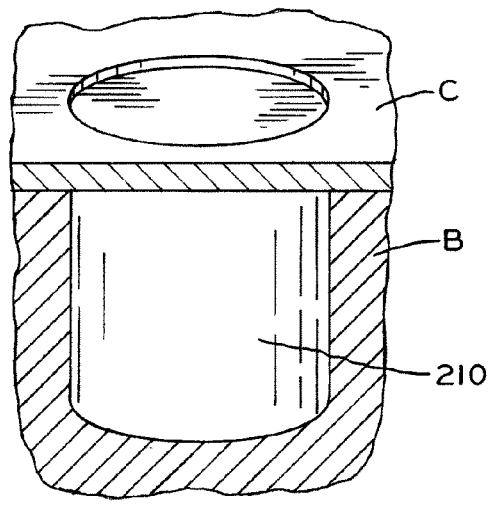
FIG. 24

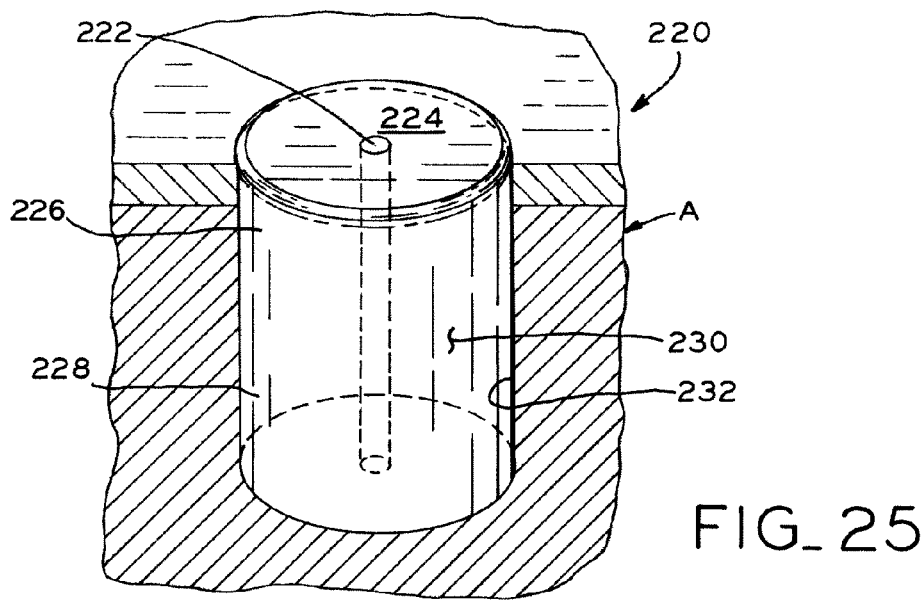
FIG_25
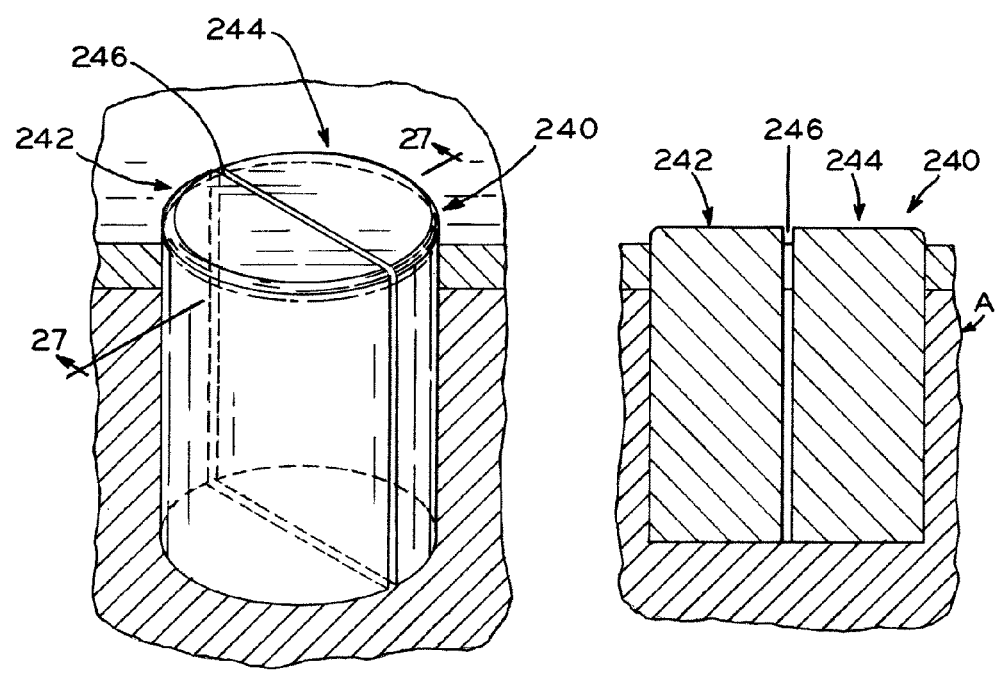
FIG_26   FIG_27

MOSAICPLASTY CONSTRUCTS

CROSS-REFERENCE TO RELATED APPLICATIONS

This application claims the benefit under Title 35, U.S.C. §119(e) of U.S. Provisional Patent Application Ser. No. 61/084,121, entitled MOSAICPLASTY CONSTRUCTS, filed on Jul. 28, 2008, the disclosure of which is expressly incorporated herein by reference.

BACKGROUND

1. Field of the Disclosure

The present disclosure relates to orthopedic implants and procedures for implanting the same. More particularly, the present disclosure relates to mosaicplasty constructs and surgical methods for implanting the same.

2. Description of the Related Art

Orthopedic implants are commonly used to replace at least a portion of a patient's joint in order to restore the use of the joint or to increase the use of the joint following deterioration due to aging or illness, disease, or injury due to trauma. Traditional orthopedic implants have been designed to replace and/or replicate the entirety of a patient's joint. However, when the area of disease and/or damage of the patient's joint is relatively small as compared to the entire joint structure, mosaicplasty implants may be used to replace and/or replicate the diseased and/or damaged portion of the patient's joint and allow the remaining, healthy portions of the joint to remain intact. For example, mosaicplasty implants may be used to replace and/or replicate a diseased and/or damaged area on the articular surface of a patient's joint. Thus, mosaicplasty implants may be used to replace diseased and/or damages portions of the articular cartilage on the articular surface of a proximal femur in a hip joint. By utilizing mosaicplasty implants, a young, athletic patient may be able to retain substantially all of their joint function.

In order to prepare a natural mosaicplasty implant, a surgeon first removes a portion of cartilage and/or bone from the diseased and/or damaged joint surface. The surgeon may then take a portion of healthy cartilage and/or bone from another location in the patient's body that will act as a mosaicplasty implant. The surgeon then prepares the area where the diseased or damaged joint surface was removed and forms the same for receipt of the mosaicplasty implant. For example, the surgeon may create a hole having a sufficient size and shape to accept the natural mosaicplasty implant. Once a sufficient hole is formed, the surgeon then implants the natural mosaicplasty implant into the hole. Exemplary procedures for preparing the cartilage and/or bone and for removing and implanting natural mosaicplasty implants are described in U.S. Pat. Nos. 6,767,354 and 7,067,123, the disclosures of which are hereby expressly incorporated herein by reference.

While natural mosaicplasty implants are effective, their underlying properties may determine their ultimate effectiveness. For example, using natural mosaicplasty implants requires removing healthy tissue from a donor site, which could cause tissue morbidity at the donor site. Additionally, due to the natural structure of a natural mosaicplasty implant, the implant may subside into the cavity over time, reducing its effectiveness as a bearing surface, or fail to be adequately retained within the cavity. Further, the limited availability of donor sites available for creating the mosaicplasty implant restricts the use of natural mosaicplasty implants to a limited number of defect areas.

SUMMARY

The present invention provides various embodiments of mosaicplasty constructs and methods for implanting the constructs into anatomical structures. The mosaicplasty constructs may be formed from artificial materials and may include a hard bearing body and a relatively softer, elastic support body. Alternatively, the mosaicplasty constructs may include a soft, elastic bearing body and a relatively harder support body. Additionally, in exemplary embodiments, the mosaicplasty constructs may also include bone ingrowth materials to facilitate ingrowth of bone and/or other tissues into the construct. In exemplary embodiments, the mosaicplasty constructs may be at least partially formed of hydrogel materials. These hydrogel materials are formulated to substantially replicate the function of a patient's natural articular cartilage. Thus, the hydrogel materials may form at least a portion of the bearing body of the mosaicplasty construct and be positioned within the anatomical structure of a patient to replicate a portion of the articular surface of a patient's joint.

Additionally, the mosaicplasty constructs of the present invention may have a specific geometry that facilitates the retention of the mosaicplasty constructs in their desired positions. For example, in one exemplary embodiment, the mosaicplasty constructs have a chamfered articulating portion. In another embodiment, the mosaicplasty constructs have a substantially rivet-shaped body. Alternatively, the mosaicplasty constructs may have a substantially hourglass-shaped body or a hemispherically-shaped bearing body. Further, in order to allow for the transfer of bodily fluids through the mosaicplasty constructs, i.e., between the articular surface of the joint and the underlying anatomical structure, the mosaicplasty constructs may have a passageway or channel formed therein. Alternatively, a gap may be formed between opposing pieces of the mosaicplasty construct.

Advantageously, by providing a mosaicplasty construct that has a bearing body that substantially replicates a patient's natural cartilage, the patient may regain substantially all of their joint function. Additionally, by utilizing bone ingrowth materials and/or designing the geometry of the mosaicplasty constructs in a manner that facilitates retention of the mosaicplasty construct in position, dislocation and/or deterioration of the mosaicplasty constructs is substantially avoided. Moreover, by forming the mosaicplasty constructs from artificial materials, the additional problems that arise during the removal and transplantation of healthy tissue are avoided.

In one form thereof, the present disclosure provides an implant for repairing a defect in a bearing surface of a bone, the bone bearing surface having a surface area, the implant including: an elastic support body sized for implantation in the bone, the elastic support body having an engagement surface, the elastic support body formed from a body material; and a bearing body having a bearing surface, the bearing surface having a surface area less than one half of the surface area of the bone bearing surface, the bearing body formed from a bearing material different than the body material.

In another form thereof, the present invention provides a method of repairing a defect in the bearing surface of a bone, the bone bearing surface having a surface area, the method including the steps of: forming an opening in the bone to receive an implant; inserting an implant into the opening, the implant including: an elastic support body having an engagement surface, the elastic support body formed from a body material; and a bearing body having a bearing surface, the bearing surface having a surface area less than one half of the surface area of the bone bearing surface, the bearing body formed from a bearing material different than the body material; and aligning a portion of the bearing body of the implant at least partially within the opening.

In yet another form there, the present invention provides an implant for repairing a defect in a bearing surface of a bone, the bone bearing surface having a surface area, the implant including: a support body sized for implantation in the bone, the support body having an engagement surface, the support body formed from a body material; and a bearing body having a bearing surface, the bearing surface having a surface area less than one half of the surface area of the bone bearing surface, the bearing body formed from a bearing material, wherein the body material and the bearing material comprise hydrogels.

In yet another form thereof, the present invention provides a method of repairing a defect in the bearing surface of a bone, the bone bearing surface having a surface area, the method including the steps of: forming an opening in the bone to receive an implant; inserting an implant into the opening, the implant including: a support body sized for implantation in the bone, the support body having an engagement surface, the support body formed from a body material; and a bearing body having a bearing surface, the bearing surface having a surface area less than one half of the surface area of the bone bearing surface, the bearing body formed from a bearing material, wherein the body material and the bearing material comprise hydrogels; and aligning a portion of the bearing body of the implant at least partially within the opening.

BRIEF DESCRIPTION OF THE DRAWINGS

The above-mentioned and other features of the invention, and the manner of attaining them, will become more apparent and will be better understood by reference to the following description of embodiments of the invention taken in conjunction with the accompanying drawings, wherein:

FIG. 11 is a partial cross-sectional exploded view of an anatomical structure and a mosaicplasty construct;

FIG. 12 is an assembled view of the mosaicplasty construct of FIG. 11 positioned at least partially within the anatomical structure of FIG. 11;

FIG. 13 is a partial cross-sectional view of an anatomical structure and a mosaicplasty construct according to a further embodiment positioned therein;

FIG. 14 is a partial cross-sectional view of an anatomical structure with the mosaicplasty construct of FIG. 13 positioned therein and deformed due to force exerted on the mosaicplasty construct by another portion of the anatomical structure;

FIGS. 21-23 are perspective views of various shapes of mosaicplasty constructs according to other embodiments;

FIG. 24 is a partial cross-sectional view of an anatomical structure with a mosaicplasty construct according to another embodiment positioned therein;

FIG. 25 is a partial cross-sectional view of an anatomical structure with a mosaicplasty construct according to another embodiment positioned therein;

FIG. 26 is a partial cross-sectional view of an anatomical structure with a mosaicplasty construct according to another embodiment positioned therein; and FIG. 27 is a cross-sectional view of the anatomical structure and mosaicplasty construct of FIG. 26 taken along line 27-27 of FIG. 26;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

The mosaicplasty constructs described herein may be implanted in a similar manner to natural or biological mosaicplasty implants, i.e., implants formed substantially entirely of materials naturally occurring in a body of a patient. Thus, the mosaicplasty constructs of the present invention may be implanted in accordance with the methods described in detail above. However, the artificial mosaicplasty constructs of the present invention can be prepared to serve a similar purpose as natural mosaicplasty implants without the use and limitations of natural tissue. Additionally, the artificial mosaicplasty constructs of the present invention are designed to provide adequate fixation of the construct to the surrounding bone. Thus, the constructs of the present invention resist the pull-out forces that may dislodge other mosaicplasty constructs, as described in detail in the Examples below.

Figure 1:
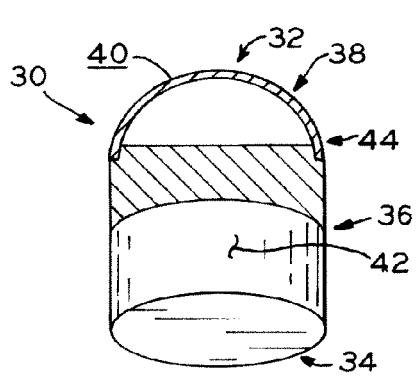
FIG. 1 is partial cross-sectional/partial perspective view of a mosaicplasty construct having a support body and a bearing body according to one embodiment, with the upper half of the support body and the bearing body shown in cross-section.

Referring now to FIG. 1, mosaicplasty construct 30 is shown and generally includes first or proximal end 32, second or distal end 34, support or elastic body 36, and bearing body 38. Mosaicplasty construct 30 has a generally cylindrically-shaped structure and may be formed from artificial components, i.e., components which are not naturally occurring in a body of a patient. As indicated above, using artificial components allows for the creation of mosaicplasty construct 30 in a manner that overcomes the limitations of using natural components. Additionally, mosaicplasty construct 30 may be formed using methods such as injection molding, compression molding, or solution casting, for example.

Bearing body 38 has a generally hemispherical shape and includes bearing surface 40. Bearing surface 40 of bearing body 38 is configured to replicate the natural articulating surface of a bone in the anatomical structure of a patient. This anatomical structure that mosaicplasty construct 30 at least partially replicates defines an articular surface area. In one exemplary embodiment, bearing surface 40 of bearing body 38 has a surface area less than one-half of the articular surface area, i.e., the area of the articular surface of the bone. In another exemplary embodiment, the surface area of bearing surface 40 is as large as $2.0\,cm^2$, $2.5\,cm^2$, $3.0\,cm^2$, $3.5\,cm^2$, or $4.0\,cm^2$, or as small as $0.10\,cm^2$, $0.25\,cm^2$, $0.5\,cm^2$, $1.0\,cm^2$, or $1.5\,cm^2$. By replicating a portion of the articular surface area of the anatomical structure, bearing surface 40 of bearing body 38 is configured to articulate against an articular surface of an opposing bone in a joint of a patient during normal joint articulation. For example, mosaicplasty construct 30 may be configured to replicate a portion of a patient's proximal femur and articulate against the patient's natural acetabulum.

In order to retain bearing body 38 in position, bearing body 38 may be connected to support body 36 at junction 44. Junction 44 may include a mechanical fixation device, such as an interlocking engagement, a snap-fit engagement, a hook and loop fastener, a biocompatible adhesive, or a groove and projection configuration, for example, that provides a connection between bearing body 38 and support body 36. Junction 44 may also include a chemical/biological fixation mechanism, such as a diffusion bond or a fiber mesh interlocking engagement, or may provide for a chemical bond between the opposing bodies. Junction 44 may also define a transition region between bearing body 38 and support body 36 when bearing body 38 is integrally formed with support body 36. In this embodiment, junction 44 defines an area of varying composition between bearing body 38 and support body 36.

In operation and after implantation in an anatomical structure, support body 36 forms a shock absorbing, elastic, and mechanical load dissipation layer that utilizes an elastic response that mimics the compressive nature of cartilage. In an exemplary embodiment, support body 36 is formed of a material having a compressive modulus that may be as small as approximately 500 kPa, 550 kPa, 600 kPa, 650 kPa, 700 kPa, or 750 kPa, or as large as approximately 1000 kPa, 950 kPa, 900 kPa, 850 kPa, or 800 kPa. Thus, bearing body 38 provides a durable bearing surface 40 which articulates against soft tissue and/or bone in the anatomical structure. Bearing surface 40 may include depressions or protrusions (not shown) therein to facilitate the creation of a liquid pocket layer at the cartilage-to-articulating surface interface, such as the structures described in U.S. patent application Ser. No. 11/684,028, entitled OPTIMIZED ARTICULAR GEOMETRY, the entire disclosure of which is hereby expressly incorporated herein by reference. Such depressions or protrusions aid in facilitating lubrication between bearing surface 40 and the articular surface of an opposing anatomical structure.

Bearing body 38 may be formed of a solid or a woven material. For example, bearing body 38 may be formed of metals such as cobalt chrome, stainless steel, titanium, or alloys thereof. Bearing body 38 may also be formed of ceramic material or surgical grade plastics. Suitable woven materials may be formed of metal fibers, plastic fibers, or synthetic fibers. Exemplary synthetic fibers include: para-aramid fibers, such as Kevlar®, available from E.I. du Pont de Nemours and Company of Wilmington, Del., U.S.A.; meta-aramid fibers, such as Nomex®, also available from E.I. du Pont de Nemours and Company of Wilmington, Del., U.S.A.; polyester; rayon; or acetate fibers. Kevlar® and Nomex® are a registered trademarks of E.I. du Pont de Nemours and Company. Bearing body 38 may be formed of a woven material similar in composition to the woven reinforcing material of an exemplary embodiment of support body 36, described in detail below.

The material used to form bearing body 38 has a strength and/or hardness greater than that of support body 36. For example, the woven material of bearing body 38 may achieve a greater strength and/or hardness relative to support body 36 by incorporating a tighter, denser weave of fibers. Alternatively, or in addition, the fibers forming bearing body 38 may be thicker and/or stronger than those forming support body 36. In an alternative embodiment, bearing body 38 may include two opposite, separate pieces that are separated by support body 36 and connected by an elastomeric cord positioned through a central aperture in support body 36 and secured to opposite bearing bodies 38. Such a construct is similar to the Dynesys® Dynamic Stabilization System commercially available from Zimmer, Inc. of Warsaw, Ind. and described in U.S. Pat. No. 7,073,415, entitled "INSTRUMENT SYSTEM FOR PEDICLE SCREWS", issued Jul. 11, 2007, the entire disclosure of which is expressly incorporated by reference herein. Dynesys® is a registered trademark of Zimmer GmbH. In an exemplary embodiment, bearing surface 40 includes a material having a Rockwell "C" hardness value as small as approximately 15, 17, 19, 21, 23, or 25, or as large as approximately 35, 33, 31, 29, or 27.

Referring again to FIG. 1, support body 38 of mosaicplasty construct 30 includes engagement surface 42 and generally defines a cylindrically-shaped structure. Support body 36 may be formed of an elastomer material, a hydrogel, and/or a woven material. In one embodiment, support body 36 is formed with an injection molded urethane, such as hydrothane AL 90A, for example. In another embodiment, support body 36 is a woven three-dimensional construct comprised of a plurality of hydrogel fibers. In this embodiment, prior to implantation, the hydrogel fibers are in a dry, i.e., dehydrated, condition and therefore allow support body 36 to be pliable and flexible. Once implanted, conformed, and/or shaped inside the anatomical structure, an aqueous solution may be introduced proximate support body 36, thereby causing the hydrogel fibers to expand and interlock support body 36 into the cavity in the anatomical structure.

The hydrogel fibers of support body 36 may be produced using polymer material such as polyacrylates (e.g. polymethacrylate, polyhydroxyethylmethacrylate (polyHEMA), and polyhydroxypropylmethacrylate), polyvinylpyrollidone (PVP), polyvinyl alcohol (PVA), polyacrylamides, polyacrylonitriles, polysaccharides (e.g. carrageenans and hyaluronic acid), polyalginates, polyethylene oxides (e.g. polyethylene glycol (PEG) and polyoxyethylene), polyamines (e.g. chitosan), polyurethanes (e.g. diethylene glycol and polyoxyalkylene diols), and polymers of ring-opened cyclic esters. The hydrogel fibers may also be formed of a combination of PVA and another polymer, such as PVP, for example. The polymers may be crosslinked by the use of photocuring, which employs radiation using ultraviolet (UV), X, or Gamma rays to create links or bonds between the polymers. The polymers may alternatively be chemical crosslinked by exposing the polymers to a crosslinking agent, for example, aqueous ion solutions. For example, aqueous ion solutions having a charge opposite that of the charged side-groups on the polymer may be used as crosslinking agents. For instance, cationic solutions of calcium, sodium, copper, aluminum, or magnesium may be used to crosslink negatively charged side-groups of the polymer. Anionic solutions of dicarboxylic acid, terphthalic acids, sulfate or carbonate may be used to crosslink positively charged side-groups on the polymer. Other suitable crosslinking agents may include dimethyl aniline, dimethylaminoethyl acetate, sodium thiosulfate, methylene bis-acrylamide, and diisothiocyanate. In general, the tensile strength of a hydrogel depends on the molecular weight of the polymers and the degree of polymerization. In addition, the swelling rate, modulus of elasticity, and viscosity are inversely related to the degree of crosslinkage between the polymers. Thus, a hydrogel having material properties desirable for a given application may be created by altering the molecular weight, degree of polymerization, and/or the degree of crosslinkage between the polymers.

In one embodiment, the hydrogel fiber construct may also act as a delivery vehicle for delivering pharmaceuticals and/or therapeutics to the anatomical structure. The hydrogel construct may contain pharmaceuticals such as antibiotics, steroids, anticoagulants, and anti-inflammatories. The hydrogel construct may also include therapeutics including growth factors, tissue response modifiers, nucleic acids/proteins, cytokines, antibodies, blood, periosteal cells (cells of the fibrous membrane covering bone), precursor tissue cells, chondrocytes, fibrocytes, and stem cells. These pharmaceuticals and therapeutics can be used to promote tissue and bone growth, promote endothelialisation, prevent fibrinosis, and fight infection. In an alternative embodiment, the hydrogel fibers may be bioresorbable and, thus, may gradually dissolve as the tissue of the anatomical structure is rebuilt.

In another embodiment, support body 36 may be formed of a reinforced hydrogel to provide added durability to mosaicplasty construct 30. The hydrogel may be reinforced by any biocompatible material including metal and/or plastic, for example. In addition, the reinforcing material may be in the form of fibers woven together to form a fabric that supports the hydrogel. The fibers of the woven material may be metal fibers formed of stainless steel, cobalt chrome, titanium, or alloys thereof. Alternatively, the fibers may include plastic fibers and/or other synthetic fibers such as: para-aramid fibers, such as Kevlar®, available from E.I. du Pont de Nemours and Company of Wilmington, Del., U.S.A.; meta-aramid fibers, such as NOMEX®, also available from E.I. du Pont de Nemours and Company of Wilmington, Del., U.S.A.; polyester; rayon; and acetate containing fibers. Kevlar® and Nomex® is a registered trademark of E.I. du Pont de Nemours and Company. The woven material may also be in the form of a molded lattice. The woven material may be coated and inundated with hydrogel. To ease implantation of support body 36, the hydrogel may be in dehydrated form such that support body 36 has a reduced size during insertion. After insertion, the dehydrated hydrogel rehydrates causing support body 36 to expand.

In operation, mosaicplasty construct 30 is implanted into a prepared cavity in an anatomical structure. The anatomical structure may include a bone layer and a cartilage layer. In some patients, however, a portion of the cartilage layer of the anatomical structure may be worn away due to disease, damage, and/or trauma. In one exemplary embodiment, mosaicplasty construct 30 is implanted in the anatomical structure such that the bulk of support body 36 is positioned in the bone layer and bearing body 38 at least partially protrudes beyond the bone layer and forms a portion of the cartilage layer, as discussed in detail above. When the anatomical structure undergoes a loading application, e.g., during articulation with an articular surface of an opposing anatomical structure, such as an opposing joint surface, bearing body 38 deflects by compressing support body 36. As a result, a cushioning and elastic supportive effect is provided by mosaicplasty construct 30 during loading applications.

Additionally, by forming bearing surface 40 of bearing body 38 to be substantially hemispherically shaped, bearing surface 40 does not undergo the same deformation as a substantially cylindrical bearing body, which is described in detail in the Examples below. Thus, mosaicplasty construct 30 may better withstand the pull-out forces experienced during joint articulation. Further, to facilitate the retention of mosaicplasty construct 30 in position, mosaicplasty construct 30 may be fixated and secured within the prepared cavity in the anatomical structure via the use of: fibrin glue; bone cement; soft tissue tabs or attachments; bone ingrowth surfaces, such as porous metal, beaded material, hydroxyapatite, or fiber metal, for example; a press fit engagement; and/or interdigitation of hydrogel material into the surrounding anatomical structure.

Figure 2:
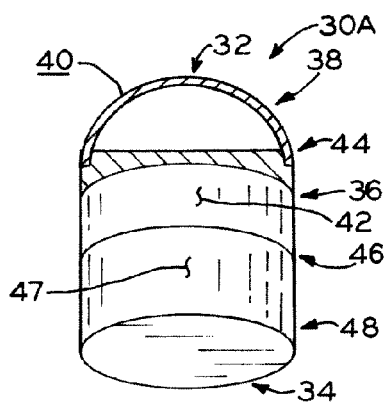
FIG. 2 is a partial cross-sectional/partial perspective view of a mosaicplasty construct according to another exemplary embodiment having a support body, a bearing body, and an attachment portion, with the upper half of the support body and the bearing body shown in cross-section.

Referring now to FIG. 2, an alternative embodiment mosaicplasty construct 30A is shown and is substantially identical to mosaicplasty construct 30, described above with reference to FIG. 1. However, mosaicplasty construct 30A differs from mosaicplasty construct 30 (FIG. 1) in that mosaicplasty construct 30A includes bone attachment portion 48 formed proximate distal end 34 thereof. Bone attachment portion 48 generally forms a cylindrically-shaped structure that has a diameter substantially similar to the diameter of support body 36. Bone attachment portion 48 may be connected to support body 36 at junction 46. Junction 46 may include a mechanical fixation device, such as an interlocking engagement, a snap-fit engagement, a hook and loop fastener, a biocompatible adhesive, or a groove and projection configuration, for example. Junction 46 may also include a chemical/biological fixation mechanism such as a diffusion bond or a fiber mesh interlocking engagement, or may provide for a chemical bond therebetween. Junction 46 may also define a transition region between bone attachment portion 48 and support body 36 when bone attachment portion 48 is integrally formed with support body 36. In an exemplary embodiment, junction 46 defines an intermeshing region in which the material of support body 36 intermeshes with the material of bone attachment portion 48. For example, if support body 36 is formed of a hydrogel and bone attachment portion 48 is formed of a porous metal, the hydrogel interdigitates or intermeshes with the porous metal such that support body 36 is interlocked with bone attachment portion 48.

As indicated above, bone attachment portion 48 may be formed from a porous material to facilitate the ingrowth of bone and other tissues into mosaicplasty construct 30A. For example, bone attachment portion 48 may be at least partially formed from a porous metal, a porous ceramic, or a woven construct. In one embodiment, bone attachment portion 48 is formed from a material having a cellular structure which resembles bone and approximates the physical and mechanical properties of bone, thereby enabling rapid and extensive soft tissue infiltration and strong attachment of bone and soft tissue structures thereto. In one exemplary embodiment, the material is a highly porous biomaterial having a porosity as low as 55, 65, or 75 percent or as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that the growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone. The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization. Such porous material facilitates ingrowth of bone and soft tissue for enhanced fixation of mosaicplasty construct 30A in an anatomical structure. For example, struts which extend from the porous structure and in combination with one another define the pores of the porous structure are generally rough. As a result, these struts facilitate the retention of a bone or soft tissue structure in such a manner that damage and disengagement of the bone or soft tissue structure is discouraged. The porous material may also have a generally corrugated surface to further facilitate biological fixation of bone and soft tissue structures thereto.

Figure 3:
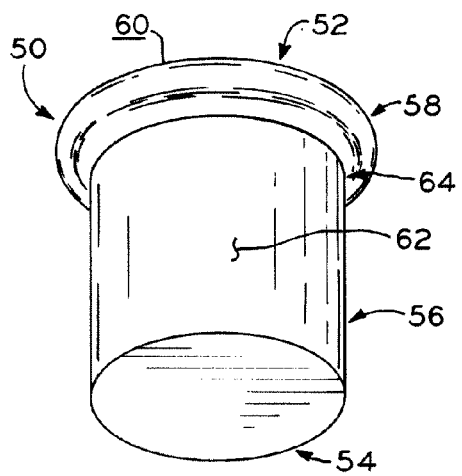
FIG. 3 is a perspective view of a mosaicplasty construct according to yet another embodiment.

Referring now to FIG. 3, an alternative embodiment mosaicplasty construct 50 is shown and is substantially identical to mosaicplasty construct 30, described above with reference to FIG. 1. However, unlike mosaicplasty construct 30, bearing body 58 of mosaicplasty construct 50 has a larger cross-sectional diameter taken perpendicular to the longitudinal axis of construct 50 than support body 56 of mosaicplasty construct 50, such that, when support bodies 36, 56 of mosaicplasty constructs 30, 50 are of equal size, bearing body 58 and bearing surface 60 of mosaicplasty construct 50 provide a larger articular or bearing surface than bearing surface 40 of mosaicplasty construct 30. Thus, in this embodiment, bearing body 58 extends outwardly beyond support body 56. In one exemplary embodiment, masociaplasty construct 50 has a shape substantially similar to a rivet, where bearing body 58 is substantially similar to the rivet's head and support body 56 is substantially similar to the rivet's body. Advantageously, by forming bearing body 58 with a larger cross-sectional diameter than support body 56, bearing body 58 has a flattened shape. As a result of the flattened shape of bearing body 58, deformation of bearing body 58, e.g., the formation of a concave depression in bearing body 58, may be prevented. In contrast, this type of deformation may be more likely to occur in entirely cylindrically-shaped mosaicplasty constructs, as described in detail in the Examples set forth below. Additionally, in one exemplary embodiment and as shown in FIG. 3, bearing body 58 may have an outwardly curving side surface extending between bearing surface 60 and junction 64.

Figure 4:
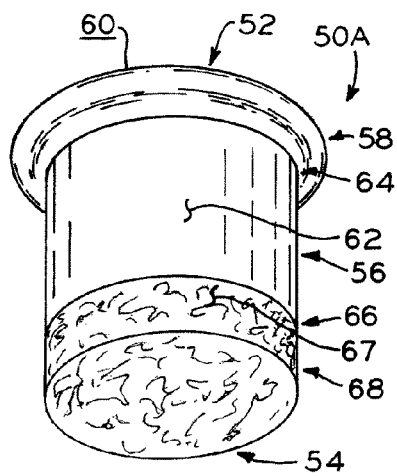
FIG. 4 is a perspective view of a mosaicplasty construct according to a further embodiment.

Referring now to FIG. 4, an alternative embodiment mosaicplasty construct 50A is shown and is substantially identical to mosaicplasty construct 50, described above with reference to FIG. 3. However, unlike mosaicplasty construct 50, mosaicplasty construct 50A includes bone attachment portion 68 formed proximate distal end 54 thereof and connected via junction 66. Bone attachment portion 68 and junction 66 are substantially identical to bone attachment portion 48 and junction 46, respectively, described above with reference to FIG. 2.

Figure 5:
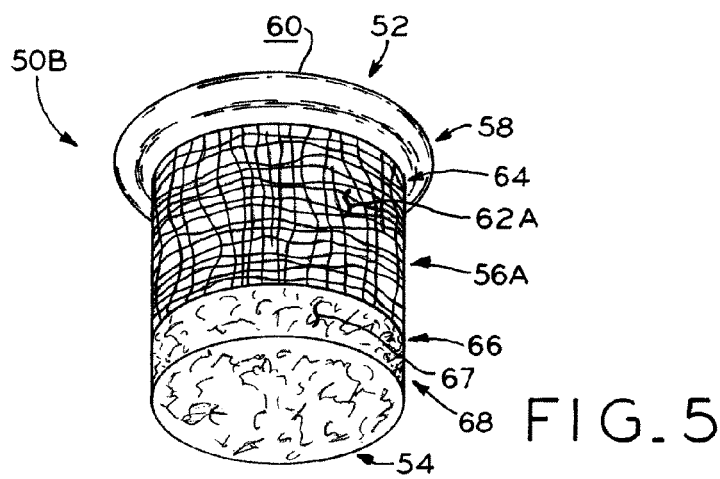
FIG. 5 is a perspective view of a mosaicplasty construct according to a still further embodiment.

Referring now to FIG. 5, an alternative embodiment mosaicplasty construct 50B is shown and is substantially identical to mosaicplasty construct 50A. However, unlike mosaicplasty construct 50A, mosaicplasty construct 50B includes support body 56A with engagement surface 62A substantially entirely defining the exterior surface of support body 56A. Support body 56A may include a plurality of woven fibers, such as hydrogel or metal fibers, that define porous engagement surface 62A. Additionally, support body 56A may be formed in a similar manner as support body 42, described in detail above with reference to FIG. 1.

Figure 6:
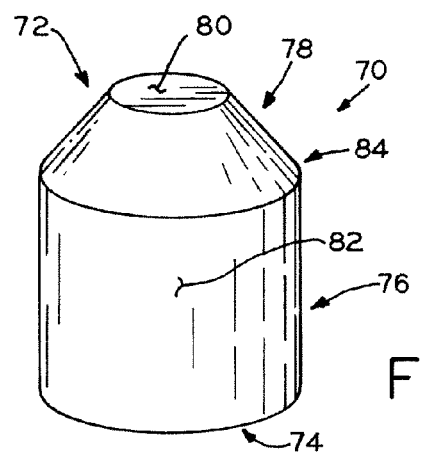
FIG. 6 is a perspective view of a mosaicplasty construct according to another embodiment.

Referring now to FIG. 6, an alternative embodiment mosaicplasty construct 70 is shown and is substantially identical to mosaicplasty construct 30, described above with reference to FIG. 1. Specifically, mosaicplasty construct 70 includes proximal end 72 and distal end 74. In one exemplary embodiment, mosaicplasty construct 30 is a one-piece construct and includes support body 76 and bearing body 78. Support body 76 and bearing body 78 may be substantially similar to support body 36 and bearing body 38, described above with reference to FIG. 1. However, in one exemplary embodiment, support body 76 and bearing body 78 are formed of a hydrogel material. For example, support body 76 and bearing body 78 may be formed of the same hydrogel material or different hydrogel materials. In one exemplary embodiment, support body 76 and bearing body 78 are formed of a hydrogel material in which support body 76 has a denser weave of hydrogel fibers than bearing body 78. As a result, bearing body 78 is more easily deformable than support body 76, as shown in FIG. 8, and deforms during articulation of a patient's joint.

Figure 7:
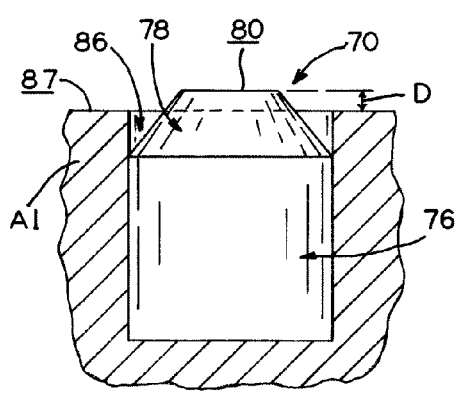
FIG. 7 is a partial cross-sectional view of an anatomical structure with the mosaicplasty construct of FIG. 6 positioned therein.
Figure 8:
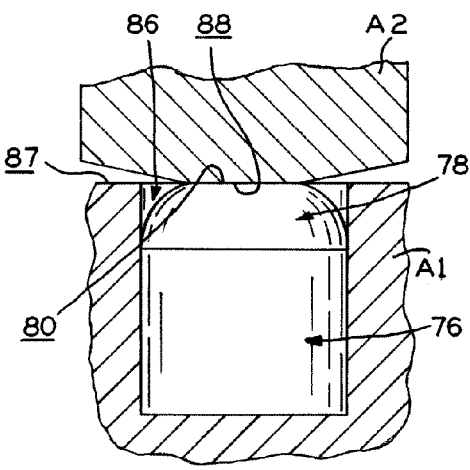
FIG. 8 is a partial cross-sectional view of an anatomical structure with the mosaicplasty construct of FIG. 6 positioned therein and deformed due to force exerted by another portion of the anatomical structure.

Referring to FIGS. 6-8, bearing body 78 includes bearing surface 80 and has a chamfered portion extending from bearing surface 80 to junction or transition region 84 defined between support body 76 and bearing body 78. In one exemplary embodiment, the chamfered portion and/or other portions of bearing body 78 may include dimples and/or other surface modifications. In another exemplary embodiment, bearing body 78 forms a truncated cone. For example, bearing body 78 may be tapered between support body 76 and bearing surface 80. As a result, when both bearing surface 80 and the bottom surface of support body 76 at distal end 74 lack dimples or other surface modifications, bearing surface 80 has a smaller surface area than the bottom surface of support body 76 at distal end 74.

Referring to FIG. 7, mosaicplasty construct 70 may be positioned at least partially within cavity 86 formed in anatomical structure A1, which may include bone and/or cartilage. Additionally, in order to facilitate the insertion of mosaicplasty construct 70 into cavity 86, mosaicplasty construct 70 may be inserted in an at least partially dehydrated state. Then, once inserted, mosaicplasty construct 70 will rehydrate and substantially fill cavity 86. For example, in one exemplary embodiment, mosaicplasty construct 70 is positioned within cavity 86 such that at least a portion of engagement surface 82 of support body 76 contacts the surrounding anatomical structure. In this embodiment, mosaicplasty construct 70 may wedge itself into the surrounding anatomical structure A1, such as trabecular bone. This may also be facilitated by the expansion of mosaicplasty construct 70 when undergoing rehydration. In another exemplary embodiment, an intermediate layer (not shown), such as a layer of bone cement, is positioned at least partially between engagement surface 82 and the portion of anatomical structure A1 defining cavity 86 to facilitate securement of mosaicplasty construct 70 therein. Additionally, mosaicplasty construct 70 may be positioned such that bearing surface 80 extends a distance D beyond bearing surface 87 of anatomical structure A1. Distance D may be as small as approximately 0.5 mm, 1.0 mm, 1.5 mm, 2.0 mm, 2.5 mm, or 3.0 mm, or as large as approximately 6.0 mm, 5.5 mm, 5.0 mm, 4.5 mm, 4.0 mm, or 3.5 mm.

Referring to FIG. 8, opposing anatomical structure A2 is shown and may include bearing surface 88. During articulation of anatomical structure A1 and anatomical structure A2, bearing surface 88 of anatomical structure A2 abuts and articulates against bearing surface 80 of mosaicplasty construct 70. Upon receiving the load imparted by anatomical structure A2, bearing body 78 deforms, e.g., compresses and expands, into the remainder of cavity 86 defined proximate the chamfered portion of bearing body 78. In one exemplary embodiment, bearing body 78 deforms into a substantially dome-shape, as shown in FIG. 8. During compression of bearing body 78, bearing body 78 expands to substantially fill cavity 86, thereby linearly increasing the contact area between bearing surface 80 and bearing surface 88. As the contact area increases, the stress on bearing body 78 decreases, until the compressive stress of the material of bearing body 78 matches the applied load, at which point deformation of bearing body 78 ceases and bearing body 78 becomes load-bearing and normal articulation may occur. The material of bearing body 78 may have a compressive modulus value such that bearing body 78 deforms until bearing surface 80 substantially matches bearing surface 87 of anatomical structure A1, thereby maintaining smooth articulation between bearing surface 88 and bearing surface 87, as well as between bearing surface 88 and bearing surface 80.

Figure 9:
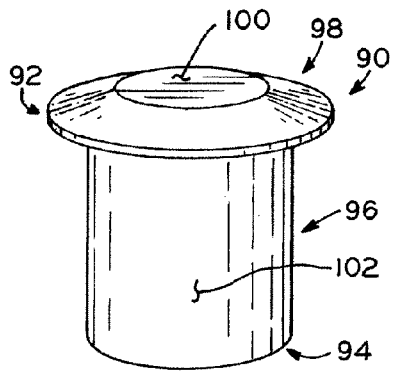
FIG. 9 is a perspective view of a mosaicplasty construct according to another embodiment.
Figure 10:
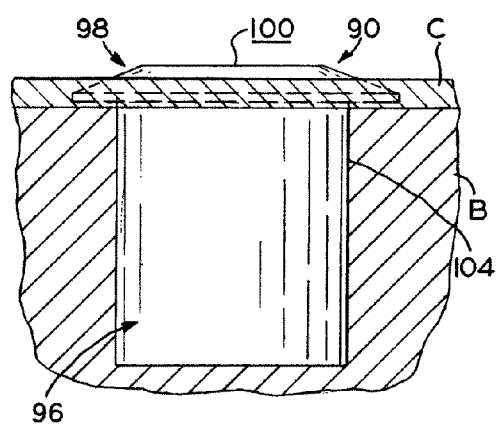
FIG. 10 is a partial cross-sectional view of an anatomical structure with the mosaicplasty construct of FIG. 9 positioned therein.

Referring now to FIGS. 9 and 10, an alternative mosaicplasty construct 90 is shown and is substantially similar to mosaicplasty constructs 50, 70, described above with reference to FIGS. 3 and 7, respectively. For example, similar to mosaicplasty constructs 50, 70, mosaicplasty construct 90 includes proximal end 92, distal end 94, support body 96, bearing body 98, bearing surface 100, and engagement surface 102. In one exemplary embodiment, bearing body 98 has a larger cross-sectional diameter perpendicular to the longitudinal axis of construct 90 than support body 96. Thus, in this embodiment, bearing body 98 extends outwardly beyond support body 96, as shown in FIG. 9, and forms a substantially rivet-shaped construct.

Referring to FIG. 9, in one exemplary embodiment, bearing body 98 includes an outer cylindrical side wall beginning at a junction formed between support body 96 and bearing body 98 and extending toward bearing surface 100. In one exemplary embodiment, the outer cylindrical side wall extends less than entirely from the junction between support body 96 and bearing body 98 to bearing surface 100. In this embodiment, bearing body 98 may further include a tapered surface extending from the proximal end of the side wall to bearing surface 100. As a result, bearing surface 100 may have a diameter smaller than the diameter of support body 96 at distal end 94.

Referring to FIG. 10, in order to implant mosaicplasty construct 90, cartilage layer C may be slightly raised, i.e., lifted a few millimeters, proximate cavity 104 in bone B and the outer edge of bearing body 98 may be positioned under the lifted portion of cartilage layer C. Specifically, outer edge of bearing body 98 may be compressed inwardly to allow it to pass through the opening in cartilage layer C. Cartilage layer C may also be slightly stretched to allow for passage of mosaicplasty construct 90 through the opening formed in cartilage layer C to position mosaicplasty construct 90 beneath cartilage layer C. Additionally, bearing body 98 may extend out of cavity 104 and above cartilage layer C and/or bone B. In this embodiment, bearing body 98 may deform during articulation of a patient's joint in a manner substantially similar to bearing body 78, described above with reference to FIG. 7. In one exemplary embodiment, bearing body 98 includes a porous material, such that cartilage layer C may grow into the pores thereof and further anchor mosaicplasty construct 90 in position. In one exemplary embodiment, only the outer, radial edge of bearing body 98 may be porous. In other embodiments, fibrin glues, tissue welding, sutures, or other similar fixation methods may be used to anchor cartilage layer C to bearing body 98. Additionally, support body 96 may include cartilage cells harvested from cartilage layer C which may be cultured in Carticel®, available from Genzyme Corporation of Cambridge, Mass., U.S.A., to encourage cartilage anchoring toward proximal end 92 of mosaicplasty construct 90. Carticel® is a registered trademark of Genzyme Corporation.

Referring now to FIGS. 11 and 12, mosaicplasty construct 110 is shown. Mosaicplasty construct 110 represents any of mosaicplasty constructs 30, 30A, 50, 50A, 50B, 70, or 90, described above, or mosaicplasty constructs 120, 140, 160, 180, 190, 200, or 210, described below. As shown in FIGS. 11 and 12, anatomical structure A defines cavity 111, which is partially filled with an injectable hydrogel formulation or acrylic polymer material 112, such as materials formed in accordance with the teachings of U.S. Pat. No. 7,485,670 to Ruberti et al., entitled SYSTEMS AND METHODS FOR CONTROLLING AND FORMING POLYMER GELS, issued on Feb. 3, 2009, the entire disclosure of which is expressly incorporated by reference herein. In other exemplary embodiments, material 112 may be a fluidized mixture of a biocompatible polymer such as a silicone or polyurethane polymer, a biocompatible hydrogel, or a biocompatible glue, such as fibrin glue, an organic glue or fibrin based adhesive material. Examples of commercially available biocompatible glues that are suitable for the present application include TISSEEL® and/or TISSUCOL® available from Immuno AG of Austria, Adhesive Protein available from Sigma Chemical, U.S.A., and Dow Corning Medical Adhesive B available from Dow Corning, U.S.A. TISSEEL® and TISSUCOL® are registered trademarks of Immuno AG.

Once positioned within cavity 111, material 112 may penetrate the cancellous bone in anatomical structure A defining cavity 111 by approximately several millimeters. Prior to material 112 gelling or setting, mosaicplasty construct 110 is inserted into cavity 111. In one exemplary embodiment, material 112 is positioned within cavity 111, such that material 112 substantially entirely lines cavity 111, as shown in FIG. 11. Additionally, referring to FIG. 11, material 112 may also be positioned to extend above cavity 111 by lining the edge of the cartilage (not shown) positioned atop anatomical structure A. In another exemplary embodiment, material 112 may be inserted directly into the bottom of cavity 111. In this embodiment, insertion of mosaicplasty construct 110 forces material 112 between the outer side surface of mosaicplasty construct 110 and the portion of anatomical structure A defining cavity 111, resulting in material 112 positioned substantially as shown in FIG. 12. In another exemplary embodiment, the exterior surface of mosaicplasty construct 110 may be treated by partial melting prior to insertion into cavity 111 to aid interpenetration of material 112 into mosaicplasty construct 110 along layer 114. Thus, once implanted, material 112 forms a mechanically-intact structure and locks mosaicplasty construct 110 in position in cavity 111 via interlocking layer 114.

Referring to FIGS. 13 and 14, mosaicplasty construct 120 is shown and may be substantially similar to mosaicplasty construct 70, described above with reference to FIGS. 6-8. Mosaicplasty construct 120 includes proximal end 122, distal end 124, support body 126, and bearing body 128. Bearing body 128 includes bearing surface 130, while support body 126 includes engagement surface 132. In one exemplary embodiment, shown in FIG. 13, mosaicplasty construct 120 has a substantially hourglass shape. Thus, in this embodiment, cross-sectional diameters of both bearing body 128 and a distal portion of support body 128 taken perpendicular to the longitudinal axis of construct 120 are greater than a cross-sectional diameter of a proximal portion of support body 128 taken perpendicular to the longitudinal axis of construct 120.

In order to receive mosaicplasty construct 120, cone-shaped cavity 134 may be formed in anatomical structure A1, which may include bone and/or cartilage. Advantageously, the cone-shape of cavity 134 aids the mechanical interlocking of mosaicplasty construct 120 with anatomical structure A1. While cavity 134 is described and depicted herein as having a cone-shape, cavity 134 may be formed in various other shapes, such as a cylindrical shape, and nothing set forth herein should be taken as limiting the configurations of cavity 134 in any manner. Once cavity 134 is formed, mosaicplasty construct 120 is positioned therein such that bearing surface 130 extends a distance D' beyond bearing surface 136 of anatomical structure A1. Distance D' may be as small as approximately 0.5 mm, 1.0 mm, 1.5 mm, 2.0 mm, 2.5 mm, 3.0 mm, 3.5 mm, 4.0 mm, 4.5 mm, or 5.0 mm or as large as approximately 10.0 mm, 9.5 mm, 9.0 mm, 8.5 mm, 8.0 mm, 7.5 mm, 7.0 mm, 6.5 mm, 6.0 mm, or 5.5 mm.

Referring to FIG. 14, opposing anatomical structure A2 is shown and may include bearing surface 138. Thus, upon articulation between anatomical structure A1 and anatomical structure A2, bearing surface 138 of anatomical structure A2 abuts and articulates against bearing surface 130 of mosaicplasty construct 120. Upon receiving the load imparted by anatomical structure A2, mosaicplasty construct 120 is compressed and expands into the remainder of cavity 134. Specifically, during compression of mosaicplasty construct 120, bearing body 128 and support body 126 deform and expand to substantially fill cavity 134. Deformation and expansion of bearing body 128 linearly increases the contact area between bearing surface 138 of anatomical structure A2 and bearing surface 130 of mosaicplasty construct 120. As the contact area increases, the stress on bearing body 128 and support body 126 decreases, until the compressive stress of the material of mosaicplasty construct 120 matches the applied load, at which point deformation ceases and mosaicplasty construct 120 becomes load-bearing, allowing normal articulation to occur.

Mosaicplasty construct 120 may have a compressive modulus that allows mosaicplasty construct 120 to compress until bearing surface 130 substantially matches or resides slightly above surface 136 of anatomical structure A1. In one exemplary embodiment, shown in FIG. 14, a portion of bearing body 128, when deformed, extends laterally beyond cavity 134 and contacts surface 136 of anatomical structure A1. In this embodiment, the portion of bearing body 128 extending beyond cavity 134 replicates the cartilage layer that is normally adjacent anatomical structure A1 and present during articulation of anatomical structure A2 against anatomical structure A1.

Figure 15:
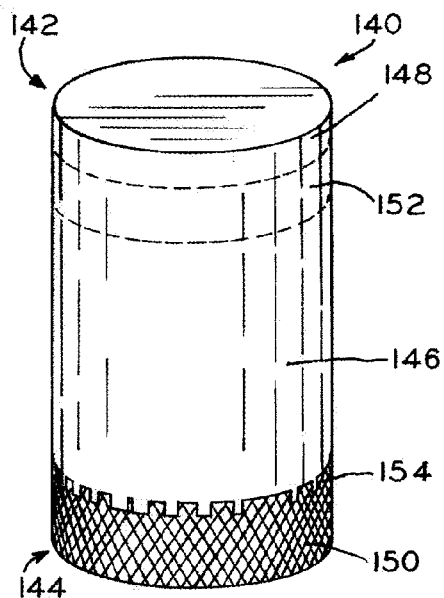
FIG. 15 is a perspective view of a mosaicplasty construct according to another embodiment.
Figure 16:
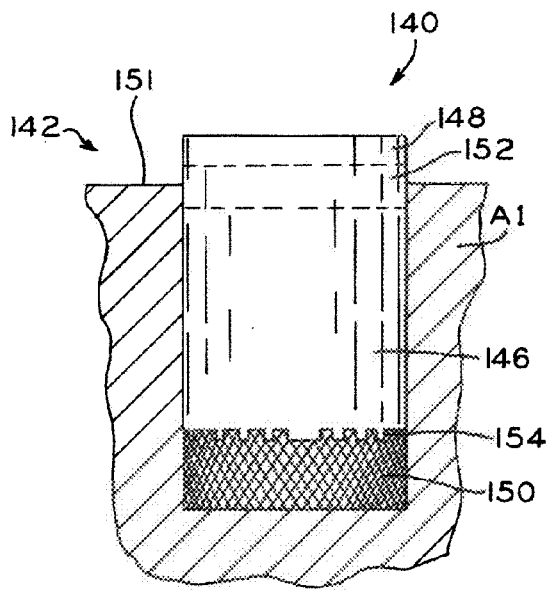
FIG. 16 is a partial cross-sectional view of an anatomical structure with the mosaicplasty construct of FIG. 15 positioned therein.

Referring to FIGS. 15 and 16, mosaicplasty construct 140 is shown. Mosaicplasty construct 140 may include proximal end 142, distal end 144, support body 146, bearing body 148, and bone attachment portion 150, which are substantially similar to corresponding components of mosaicplasty construct 30A, shown in FIG. 2. As shown in FIG. 16, mosaicplasty construct 140 may be positioned in anatomical structure A1 such that bearing body 148 at least partially extends beyond surface 151 of anatomical structure A1 in a substantially similar manner as described in detail above with reference to mosaicplasty construct 120. However, the various components of mosaicplasty construct 140 may be formed in a different manner than the various components of other mosaicplasty constructs described herein.

Specifically, in one exemplary embodiment of mosaicplasty construct 140, bearing body 148 is formed of a hydrogel material, such as PVA. The surface of the hydrogel material forming bearing body 148 may be highly porous upon fabrication or may be initially reinforced with a resorbable second phase contained within the hydrogel continuous phase. In one exemplary embodiment, support body 146 is formed of a polymer having a higher compressive modulus than the hydrogel material of bearing body 148, such as ethylene vinyl alcohol (EVaL), and bone attachment portion 150 is formed of a porous metal, such as a metal formed using Trabecular Metal™ technology. In this embodiment, the higher compressive modulus polymer of support body 146 provides for mechanical integrity with the porous metal of bone attachment portion 150, while the hydrogel of bearing body 148 provides a lubricious, low wear bearing surface. In other embodiments, bone attachment portion 150 may be formed from an allograft plug, from porous ceramic, or from a porous, rigid plastic.

As shown in FIG. 15, mosaicplasty construct 140 includes transition region 152 which is positioned between bearing body 148 and support body 146. In one exemplary embodiment, transition region 152 defines an area of mosaicplasty construct 140 within which the hydrogel forming bearing body 148 and the polymer forming support body 146 are intermixed with one another. Specifically, the relative concentrations of the hydrogel of bearing body 148 and the polymer of support body 146 will increase and decrease depending on the proximity of a particular area of transition region 152 to bearing body 148 and support body 146. In one exemplary embodiment, the concentration of the hydrogel of bearing body 148 that forms transition region 152 increases as transition region 152 approaches bearing body 148. In contrast, the concentration of the polymer of support body 146 that forms transition region 152 decreases as transition region 152 approaches bearing body 148. Similarly, the concentration of the polymer of support body 146 that forms transition region 152 increases as transition region 152 approaches support body 146. In contrast, the concentration of the hydrogel of bearing body 148 that forms transition region 152 decreases as transition region 152 approaches support body 146. In another exemplary embodiment, transition region 152 may further include a biocompatible elastomer. In one exemplary embodiment, the gradient in material properties throughout mosaicplasty construct 140 and transition region 152 may be achieved by forming the entirety of mosaicplasty construct 140 from a hydrogel material. For example, mosaicplasty construct 140 may be formed from a hydrogel material having a gradient in material properties due to nonuniform solvent, chemical, or radiation treatment of the hydrogel material. Additionally, the gradient in material properties provided using a hydrogel material may extend in either direction through mosaicplasty construct 140. Thus, in one embodiment, mosaicplasty construct 140 decreases in rigidity from bearing body 148 to bone attachment portion 150. In another exemplary embodiment, mosaicplasty construct 140 increases in rigidity from bearing body 148 to bone attachment portion 150.

In one exemplary embodiment, the polymer of support body 146 is connected to the porous metal of bone attachment portion 150 by interdigitation therewith. Specifically, the polymer of support body 146 is injected into or otherwise received within the pores of the porous metal of bone attachment portion 150. This allows the polymer to interdigitate with the pores of the porous metal, bonding the polymer to the porous metal due to the interference between the polymer and the portions of the porous metal that surround the interdigitated polymer. This area of interdigitation of the polymer of support body 146 with the porous metal of bone attachment portion 150 extends along transition region 154, as shown in FIGS. 15 and 16. Additionally, while mosaicplasty construct 140 is shown in FIGS. 15 and 16 as having a substantially cylindrical shape, mosaicplasty construct 140 may, alternatively, have a shape substantially similar to any other mosaicplasty construct described herein.

Figure 17:
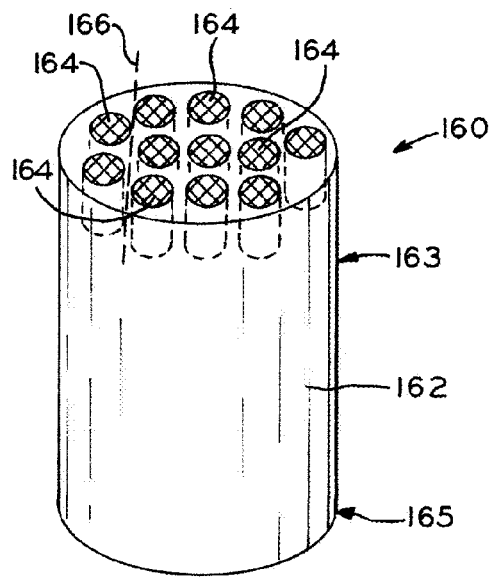
FIG. 17 is a perspective view of a mosaicplasty construct according to another embodiment.

Referring now to FIG. 17, mosaicplasty construct 160 is shown according to another exemplary embodiment and is rotated 180 degrees from the other mosaicplasty constructs depicted herein to facilitate illustration. Mosaicplasty construct 160 includes body 162 having support body 163 and bearing body 165. Contained at least partially within support body 163 are a plurality of porous metal disks 164. Porous metal disks 164 may be interconnected or may exist as separate structures within body 162. In an exemplary embodiment, support body 163 is formed of a hydrogel material and porous metal disks 164 are formed of a porous metal formed using Trabecular Metal™ technology, as discussed in detail above. In another exemplary embodiment, disks 164 may be formed from materials known to induce bony ingrowth, such as hydroxyapetite loaded particles. Additionally, in one exemplary embodiment, the hydrogel defining body 162 may be inserted as a hydrogel pre-cursor formulation that is injected as a liquid and then gels in situ.

Disks 164 may be arranged such that preferred cut lines, such as cut line 166, are maintained through body 162 so that mosaicplasty construct 160 may be trimmed to a desired size prior to implantation in an anatomical structure. Specifically, a surgeon may trim away portions of mosaicplasty construct 160 along the preferred cut lines, such as cut line 166, in a direction along the longitudinal axis of construct 260 without contacting any of disks 164. Mosaicplasty construct 160 may be substantially cylindrically-shaped or may be shaped similar to any other mosaicplasty construct described herein. Disks 164 may also be provided on the side walls of support body 163 and may be positioned such that disks 164 abut a bone surface upon implantation of mosaicplasty construct 160.

Figure 20:
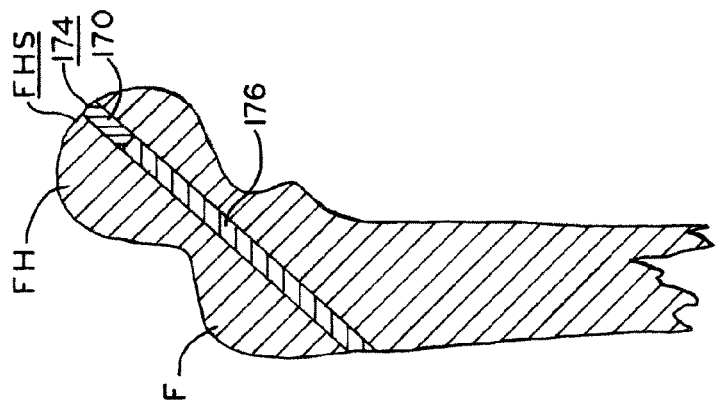
FIG. 20 is yet another partial cross-sectional view of the proximal femur of FIG. 18, illustrating yet another step in the procedure for implanting a mosaicplasty construct.
Figure 19:
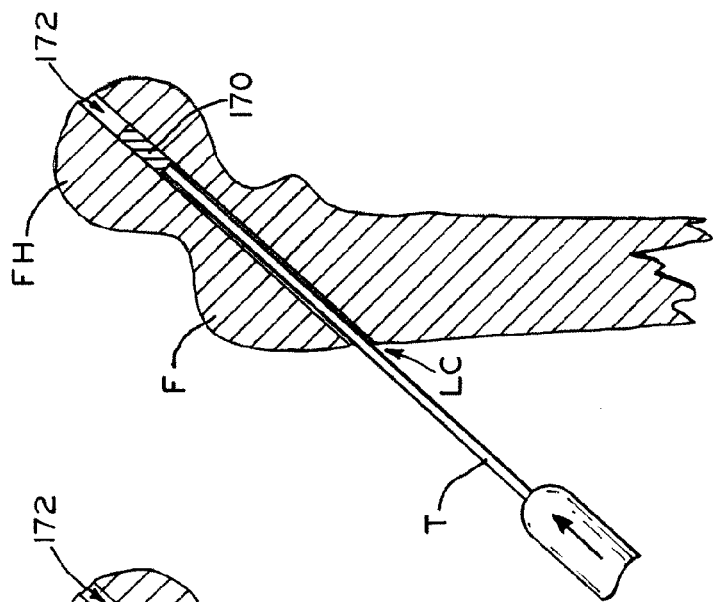
FIG. 19 is another partial cross-sectional view of the proximal femur of FIG. 18, illustrating another step in the procedure for implanting a mosaicplasty construct.
Figure 18:
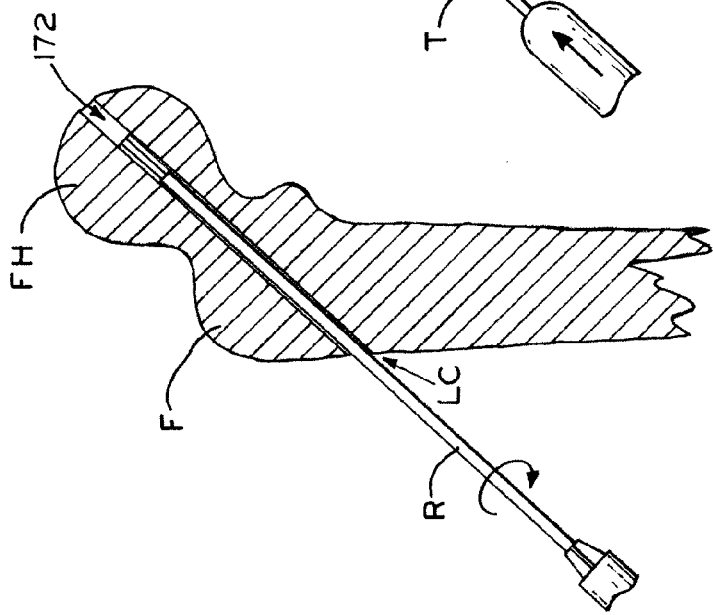
FIG. 18 is a partial cross-sectional view of a proximal femur, illustrating a first step in a procedure for implanting a mosaicplasty construct.

Referring now to FIGS. 18-20, an exemplary method of implanting any of the mosaicplasty constructs described herein is shown. As shown in FIG. 18, reamer R may be used to drill a hole through femur F from a location proximate lateral cortex LC of femur F and through femoral head FH of femur F to form elongated cavity 172. While described and depicted herein with specific reference to a femur, the present invention may be used in conjunction with any bone that has a hyaline or articular cartilage layer, such as a humerus, and nothing herein should be taken as limiting the scope of the invention in any manner. Referring to FIG. 19, tool T may be used to push mosaicplasty construct 170 through elongated cavity 172 from lateral cortex LC to femoral head FH until mosaicplasty construct 170 is positioned at least partially within cavity 172. In one exemplary embodiment, mosaicplasty construct 170 is positioned with bearing surface 174 substantially flush with femoral head surface FHS of femoral head FH, as shown in FIG. 20. In another exemplary embodiment, mosaicplasty construct 170 is positioned with bearing surface 174 extending beyond femoral head surface FHS of femoral head FH, i.e., extending out of cavity 172. Referring again to FIG. 20, bone cement, bone graft, or other suitable biocompatible filler material 176 may be used to fill the remainder of cavity 172. With the method shown in FIGS. 18-20, the synovial membrane and the capsule of the hip joint may be preserved and undisturbed. Mosaicplasty construct 170 may be substantially similar to any or all mosaicplasty constructs described herein.

In another exemplary embodiment for implantation of any of the mosaicplasty constructs described herein, the mosaicplasty construct is advanced into a hollow, tapered inserter (not shown). As the mosaicplasty construct is advanced through the inserter, it is compressed by the tapered walls of the inserter. Specifically, the mosaicplasty construct is compressed to have a diameter smaller than the diameter of the defect cavity formed in an anatomical structure. Thus, by positioning the smaller diameter end of the inserter in the defect cavity, the mosaicplasty construct can be pushed out of the smaller diameter end of the inserter allowing the mosaicplasty construct to expand. The expansion of the mosaicplasty construct will cause it to contact the portion of the anatomical structure defining the defect cavity and form a press-fit between the mosaicplasty construct and the anatomical structure that fixes the mosaicplasty construct in position.

FIGS. 21-23 illustrate different cross-sectional shapes in which any of the mosaicplasty constructs described herein may be formed. Specifically, FIG. 21 depicts mosaicplasty construct 180 having a substantially rectangular cross-section. FIG. 22 depicts mosaicplasty construct 190 having a substantially triangular cross-section, and FIG. 23 depicts mosaicplasty construct 200 having a substantially elongated "plus" or cross-shape cross-section.

Referring to FIG. 24, mosaicplasty construct 210 is shown positioned in bone B. Mosaicplasty construct 210 may be substantially similar to any or all of the mosaicplasty constructs described herein. However, in contrast to the other mosaicplasty constructs described herein, mosaicplasty construct 210 is formed as a relatively rigid support and is designed to reinforce and/or support, instead of replace, an existing hyaline or articular cartilage layer. For example, mosaicplsaty construct 210 may be used to treat non-critical cartilage defects, e.g., defects of less than 1 cm², by removing the diseased and/or damaged subchondral bone beneath the cartilage and replacing it with mosaicplasty construct 210. To facilitate treatment, the rigid support material may be positioned substantially flush with the surface of bone B. In this position, mosaicplasty construct 210 underlies at least a portion of cartilage C and provides support to cartilage C. Mosaicplasty construct 210 may be implanted using any of the methods described herein. Additionally, in another exemplary embodiment, cartilage C is arthroscopically retracted, a cavity is drilled in bone B, and mosaicplasty construct 210 is implanted into the cavity formed in bone B. Irrespectively of the implantation method used, once implanted, cartilage C may be sutured or fibrin glued to bone B and/or mosaicplasty construct 210.

Referring to FIG. 25, another exemplary mosaicplasty construct is shown as mosaicplasty construct 220. Mosaicplasty construct 220 may be formed in a manner substantially similar to any other mosaicplasty construct described herein. However, unlike the other mosaicplasty constructs, mosaicplasty construct 220 includes a central bore 222 extending from bearing surface 224 of bearing body 226 and ending at the opposing surface of mosaicplasty construct 220 at support body 228. Thus, central bore 222 extends entirely through mosaicplasty construct 220. While described and depicted herein as a central bore, bore 222 may be positioned to extend through bearing surface 224 at any point thereon. Additionally, bore 222 may extend less then entirely along the longitudinal length of mosaicplasty construct 220. For example, bore 222 may start at bearing surface 224 and end at cylindrical side surface 230. In another exemplary embodiment, mosaicplasty construct 220 may be formed of a porous material having at least one series of interconnected pores with no dead ends, which provides for fluid communication between exterior surfaces of mosaicplasty construct 220.

Advantageously, the use of bore 222 allows for fluid to flow to and from bearing surface 224 and cavity 232 formed in anatomical structure A1. By providing for fluid flow between bearing surface 224 and cavity 232, the articulation of an opposing anatomical structure upon bearing surface 224 will force fluid through mosaicplasty construct 220. Then, once the force of the opposing anatomical structure is lessened, fluid may be drawn to bearing surface 224 through bore 222 of mosaicplasty construct 220. As a result of the flow of fluid through bore 222, the likelihood of mosaicplasty construct 220 becoming locked to the opposing anatomical structure due to the creation of a difference in fluid pressure, e.g., acting as a suction cup against the opposing anatomical structure, is substantially reduced.

Referring to FIG. 26, another exemplary mosaicplasty construct is shown as mosaicplasty construct 240. Mosaicplasty construct 240 may be formed in a manner substantially similar to any other mosaicplasty construct described herein. However, unlike the other mosaicplasty constructs, mosaicplasty construct 240 is formed as two individual portions 242, 244 having gap 246 therebetween. Each of portions 242, 244 forms a half of mosaicplasty construct 240. While described and depicted herein as forming halves of mosaicplasty construct 240, portions 242, 244 may form differing amounts of mosaicplasty construct 240, such as portion 242 forming 75 percent of the volume of mosaicplasty construct 240 and portion 244 forming 25 percent of the volume of mosaicplasty construct 240.

Advantageously, by forming gap 246 between portions 242, 244 of mosaicplasty construct 240, fluid is allowed to flow therebetween. By providing for fluid flow between portions 242, 244 of mosaicplasty construct 240, the articulation of an opposing anatomical structure upon mosaicplasty construct 240 will force fluid through gap 246. Then, once the force of the opposing anatomical structure is lessened, fluid may be drawn upward through gap 246 of mosaicplasty construct 240. As a result of the flow of fluid through gap 246, the likelihood of mosaicplasty construct 240 becoming locked to the opposing anatomical structure due to the creation of a difference in fluid pressure, e.g., acting as a suction cup against the opposing anatomical structure, is substantially reduced.

Although described throughout with varying shapes and fixation mechanisms, any or all of the mosaicplasty constructs described herein may include tabs or shapes to prevent the mosaicplasty construct from rotating relative to the cavity in the anatomical structures in which the mosaicplasty constructs are positioned.

EXAMPLES

The following non-limiting Examples illustrate various features and characteristics of specific mosaicplasty implant designs, but is not to be construed as limited thereto. The following abbreviations are used throughout the Examples unless otherwise indicated.

TABLE 1

Abbreviations

| Abbreviation | Full Word |
| --- | --- |
| PVA | poly(vinyl alcohol) |
| MW | molecular weight |
| PEG | poly(ethylene glycol) |
| ° | degree |
| C. | Celsius |
| mm | millimeter |
| H | height |
| W | width |
| D | depth |
| POD | pin-on-disc |
| u | atomic mass constant |
| Hz | hertz |

Example 1

Effect of Cyclic Articulation on a Cylindrical Hydrogel Implant

The effect of cyclic articulation on a cylindrical hydrogel implant was tested. A PVA, having a molecular weight of 115,000 u, was obtained in the form of an aqueous solution. The PVA was then mixed with PEG, having a molecular weight of 400 u, obtained from Acros Organics, having a principal place of business in Geel, Belgium. The PVA was mixed with the PEG at about 90° C. to form an aqueous solution having a 10% PVA-25% PEG concentration. The hot mixture was then cast into square glass molds with glass slide covers that were heated to approximately 90° C. to form hydrogel sheets measuring 5 mm H×25 mm D×45 mm W. After one day of gelling at room temperature, the molded hydrogel sheets were cut into cylindrical hydrogel plugs using Corneal trephine blades having a diameter of 6.0 mm mounted on an Enco drill press Model 105-1100. Corneal trephine blades are available from Stradis Healthcare of Alpharetta, Ga. and Enco drill presses Model 105-1100 are available from Enco Manufacturing Co. of Chicago, Ill.

Figure 28:
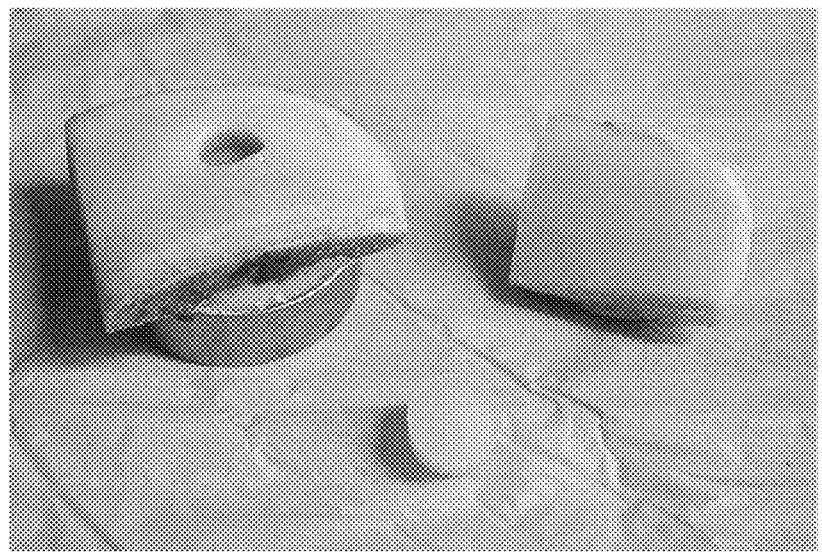
FIG. 28 is a photograph of the individual test components used in conjunction with Example 1.

An adult cow knee (left side) was used for the animal POD model. X-rays confirmed that the knee had good bone stock. The soft tissue around the patella and distal femur was removed. Subsequently, two cartilage specimens, i.e., a cartilage on disk and a cartilage on pin specimen, each measuring 30 mm by 15 mm by 15 mm, were cut out of the trochlear groove with a bandsaw and were used as an articular pair on a bi-directional POD wear tester. Specifically, the subchondral bone on the backside of the cut pieces of the cartilage was roughened with a drill and cemented onto stainless steel holders using bone cement. The stainless steel holders were then attached to the POD wear tester and loaded to determine the contact area between the two cartilage specimens. The individual test components are depicted in FIG. 28.

Figure 29:
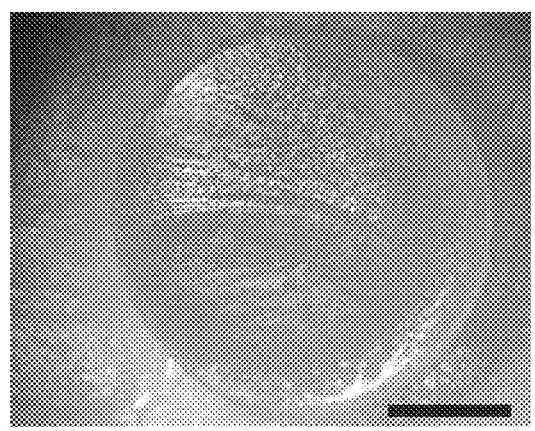
FIG. 29 is a photograph of a hydrogel plug positioned within and extending partially from a cartilage specimen taken from directly above the hydrogel plug.

The cartilage specimens were then removed from the wear tester and a defect was created on the top of the cartilage specimens within the contact area of the cartilage. The defect was formed using a 5.5 mm diameter drill bit followed by a flat bottom drill to form an approximate 5 mm deep cylindrical cavity. The hydrogel plugs were then positioned within the cartilage specimens. The starting hydrogel plugs were slightly tapered with a larger top diameter, which was approximately 6 mm, and a smaller bottom diameter, which was greater than 5 mm but less than 6 mm. The hydrogel plugs used were soft and temporarily deformed during trephine cutting, as described above, resulting in the tapered shape of the plug. The tapered shape prohibited the hydrogel plugs from fully seating into the bottom of the cavity in the cartilage specimens, which lead some portion of the hydrogel plugs protruding from the surrounding cartilage surface by about 1 mm, as shown in FIG. 29.

A bottom cartilage piece, against which the hydrogel plugs articulated during testing, and the cartilage containing the hydrogel plugs were then mounted on the bi-directional POD wear tester, which was actuated on a 5 mm×10 mm rectangular track by a X-Y table, available form Parkers Systems of Rohnert Park, Calif., as described below. The wear test was run in an 100% bovine serum environment. Prior to the test, the serum was mixed with penicillin-streptomycin to delay bacterial growth and to protect the cartilage. The X-Y table was then mounted on an MTS servo-hydraulic testing machine, available from MTS of Minneapolis, Minn. The MTS machine was programmed to produce a Paul-type curve in synchronization with the motion of the XY table. A Paul-type curve is explained in detail in *Forces Transmitted By Joints in the Human Body* by J. P. Paul and published in the Proceedings Institution of Mechanical Engineers at Vol. 181, Part 37, pages 8-15, the entire disclosure of which is expressly incorporated by reference herein. The peak load of the Paul-type loading curve corresponded to a peak contact pressure of 30 lbf between each of the cartilage specimens and the bottom cartilage piece. Tests were conducted at 0.5 Hz to a total of 1,000 cycles.

Figure 30:
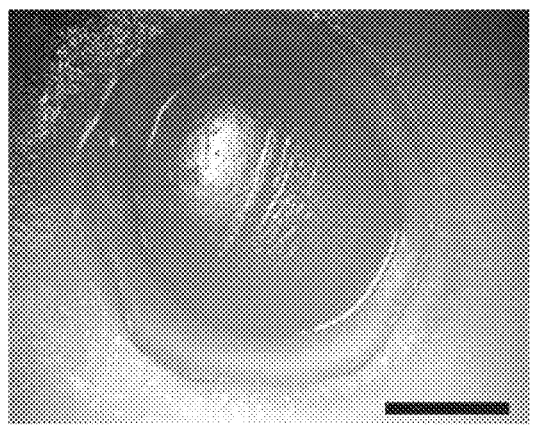
FIG. 30 is a photograph of the hydrogel plug and cartilage specimen of FIG. 29 taken after the completion of 1,000 pin-on-disc wear cycles.

After 1000 cycles of POD testing, the protruded portion of the hydrogel plugs became flattened with a flare-like flap and concave groove along the periphery of the cavity opening, as shown in FIG. 30. Additionally, when the opposing cartilage piece was lifted from the hydrogel-imbedding cartilage surface, the hydrogel plugs were pulled out of the cavity due to the suction on the opposing surface resulting form the flattened shape of the hydrogel plugs.

Example 2

Effect of Cyclic Articulation on a Cylindrical Hydrogel Implant

The effect of cyclic articulation on a cylindrical hydrogel implant was tested. A PVA, having a molecular weight of 115,000 u, was obtained in the form of an aqueous solution. The PVA was then mixed with PEG, having a molecular weight of 400 u, obtained from Acros Organics, having a principal place of business in Geel, Belgium. The PVA was mixed with the PEG at about 90° C. to form an aqueous solution having a 10% PVA-25% PEG concentration. The hot mixture was then cast into square glass molds with glass slide covers that were heated to approximately 90° C. to form hydrogel sheets measuring 5 mm H×25 mm D×45 mm W. After one day of gelling at room temperature, the molded hydrogel sheets were cut into cylindrical hydrogel plugs using Corneal trephine blades having a diameter of 6.0 mm mounted on an Enco drill press Model 105-1100. Corneal trephine blades are available from Stradis Healthcare of Alpharetta, Ga. and Enco drill presses Model 105-1100 are available from Enco Manufacturing Co. of Chicago, Ill.

An adult cow knee (left side) was used for the animal POD model. X-rays confirmed that the knee had good bone stock. The soft tissue around the patella and distal femur was removed. Subsequently, two cartilage specimens, i.e., a cartilage on disk and a cartilage on pin specimen, each measuring 30 mm×15 mm×15 mm were cut out of the trochlear groove with a bandsaw and were used as an articular pair on a bi-directional POD wear tester. Specifically, the subchondral bone on the backside of the cut pieces of the cartilage was roughened with a drill and cemented onto stainless steel holders using bone cement. The stainless steel holders were then attached to the POD wear tester and loaded to determine the contact area between the two cartilage specimens. The individual test components were substantially similar to those depicted in FIG. 28 with respect to Example 1 above.

Figure 31:
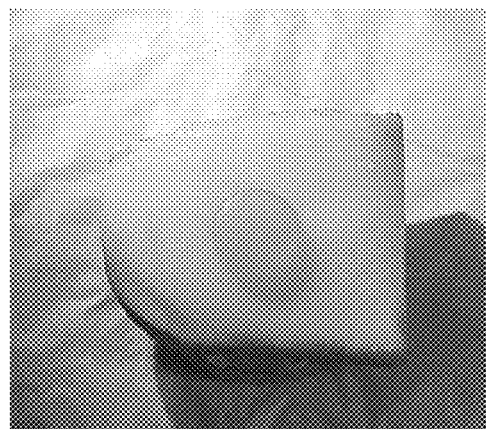
FIG. 31 is another photograph of a hydrogel plug positioned within and extending partially from a cartilage specimen.
Figure 32:
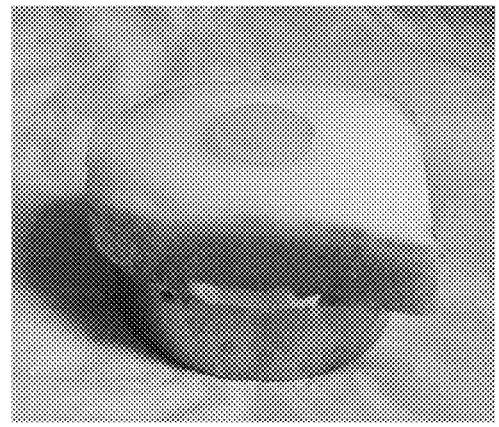
FIG. 32 is a photograph of the hydrogel plug and cartilage specimen of FIG. 31.

The cartilage specimens were then removed from the wear tester and a defect was created on the top of the cartilage on disk specimens within the contact area of the cartilage. The defect was formed using a 9.5 mm diameter drill bit followed by a flat bottom drill to form an approximate 5.3 mm deep cylindrical cavity. The hydrogel plugs were hydrated in bovine serum at room temperature prior to testing. The hydrogels plugs were then positioned within the cartilage specimens. The starting hydrogel plugs were slightly tapered with a larger top diameter, which was approximately 11 mm, and a smaller bottom diameter, which was greater than 10 mm but less than 11 mm. The hydrogel plugs used were soft and temporarily deformed during trephine cutting, as described above, resulting in the tapered shape of the plug. The tapered shape prohibited the hydrogel plugs from fully seating into the bottom of the cavity in the cartilage specimens, which lead some portion of the hydrogel plug protruding from the surrounding cartilage surface by about 1 mm, as shown in FIGS. 31 and 32, below.

A bottom cartilage piece, against which the hydrogel plugs articulated during testing, and the cartilage containing the hydrogel plugs were then mounted on the bi-directional POD wear tester, which was actuated on a 5 mm×10 mm rectangular track by a X-Y table, available from Parkers Systems of Rohnert Park, Calif., as described below. The wear test was run in an 100% bovine serum environment. Prior to the test, the serum was mixed with penicillin-streptomycin to delay bacterial growth and to protect the cartilage. The X-Y table was then mounted on an MTS servo-hydraulic testing machine, available from MTS of Minneapolis, Minn. The MTS machine was programmed to produce a Paul-type curve in synchronization with the motion of the XY table. A Paul-type curve is explained in detail in *Forces Transmitted By Joints in the Human Body* by J. P. Paul and published in the Proceedings Institution of Mechanical Engineers at Vol. 181, Part 37, pages 8-15. The peak load of the Paul-type loading curve corresponded to a peak contact pressure of 30 lbf between each of the cartilage specimens and the bottom cartilage piece. Tests were conducted at 0.5 Hz to a total of 1,000 cycles.

Figure 33:
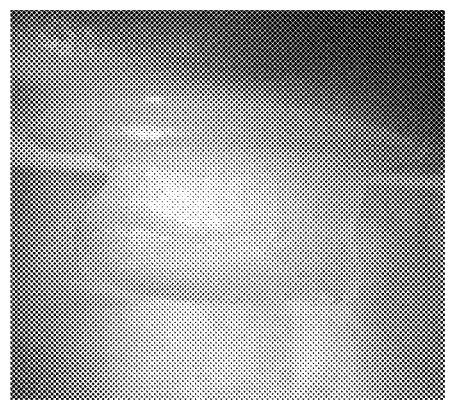
FIGS. 33-36 are photographs of the hydrogel plug and cartilage specimen of FIG. 31 taken after the completion of 1,000 pin-on-disc wear cycles.
Figure 34:
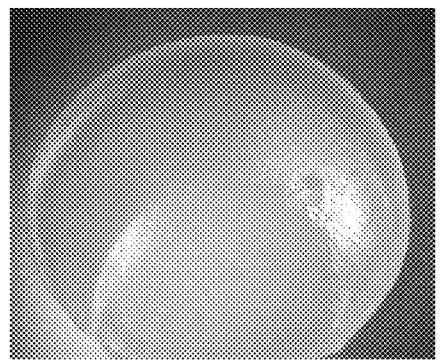
Figure 35:
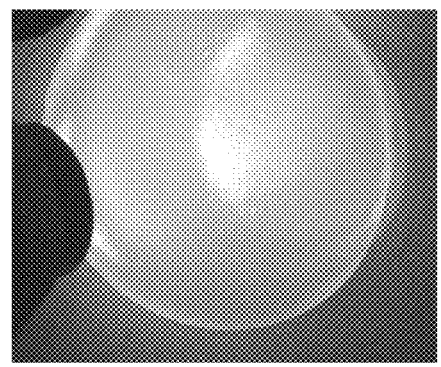
Figure 36:
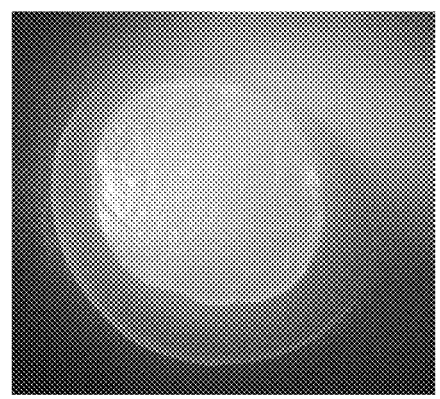

After 1000 cycles of POD testing, when the opposing cartilage piece was lifted from the hydrogel-imbedding cartilage surface, the hydrogel plugs adhered on the cartilage surface due to the suction onto the opposing surface and were pulled out of the cavity, as shown in FIG. 33. As shown, the top surface of the plugs still adhered to the opposing cartilage due to suction. As shown in FIGS. 34 and 35, the protruded portion of the hydrogel plugs prior to the POD test became flattened into a thick flap leaning toward one direction unlike the case in Example 1 where the flap was substantially entirely around the cavity opening. The bottom view of the pulled out hydrogel plug, shown in FIG. 36, clearly shows that the flap was not formed all around the periphery of the plug top surface, but only covered approximately ⅔ of it.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An implant for repairing a defect at a bearing surface of a bone, the implant comprising:
   an elastic support body formed of a body material and sized for implantation in the bone, said elastic support body having an exterior configured to engage bone or cartilage, the exterior comprising a porous engagement surface;
   a bearing body extending from said elastic support body and having a bearing surface configured to articulate against an opposing bone, said bearing surface having a generally hemispherical shape, and said bearing body formed from a bearing material different than said body material, wherein said bearing material has a strength greater than a strength of said body material; and
   a porous bone attachment portion extending from said elastic support body in a direction substantially opposite said bearing body and including a porous tantalum structure, wherein said bone attachment portion is sized for implantation in the bone and has a generally cylindrical shape.

2. The implant of claim 1, wherein said porous engagement surface comprises a plurality of woven fibers.

3. An implant for repairing a defect at a bearing surface of a bone, the implant comprising:
   an elastic support body sized for implantation in the bone, said elastic support body having an engagement surface, said elastic support body formed from a body material;
   a bearing body extending from said elastic support body and having a bearing surface configured to articulate against an opposing bone, said bearing surface having a generally hemispherical shape and a surface area of less than 2.0 cm$^2$, and said bearing body formed from a bearing material different than said body material, wherein said bearing material has a strength greater than a strength of said body material; and
   a porous bone attachment portion extending from said elastic support body in a direction substantially opposite said bearing body and including a porous tantalum structure, wherein said bone attachment portion is sized for implantation in the bone and has a generally cylindrical shape.

4. The implant of claim 3, wherein said body material comprises at least one of a hydrogel material, an elastomeric material, a polymer material, and a porous material.

5. The implant of claim 3, wherein said body material comprises a material having a compressive modulus between approximately 500 kPa and approximately 1000 kPa.

6. The implant of claim 5, wherein said body material comprises a material having a compressive modulus between approximately 700 kPa and approximately 800 kPa.

7. The implant of claim 3, wherein said bearing material comprises a material having a Rockwell C hardness value between approximately 15 and 35.

8. The implant of claim 7, wherein said bearing material comprises a material having a Rockwell C hardness value between approximately 25 and 35.

9. The implant of claim 3, wherein said bearing body has a bearing body cross-section perpendicular to the longitudinal axis of the implant and said elastic support body has an elastic support body cross-section perpendicular to the longitudinal axis of the implant, wherein said bearing body cross-section is smaller than said elastic support body cross-section.

\* \* \* \* \*